United States Patent
Goel et al.

(10) Patent No.: US 10,577,613 B1
(45) Date of Patent: Mar. 3, 2020

(54) ENGINEERED CELL LINES FOR INCREASED PROTEIN PRODUCTION

(71) Applicant: Celltheon Corporation, Union City, CA (US)

(72) Inventors: Amita Goel, Union City, CA (US); Nikhil Goel, Union City, CA (US)

(73) Assignee: Celltheon Corporation, Union City, CA (US)

( * ) Notice: Subject to any disclaimer, the term of this patent is extended or adjusted under 35 U.S.C. 154(b) by 0 days.

(21) Appl. No.: 15/351,043

(22) Filed: Nov. 14, 2016

Related U.S. Application Data

(60) Provisional application No. 62/255,306, filed on Nov. 13, 2015.

(51) Int. Cl.
*C12N 15/85* (2006.01)
*C12N 15/67* (2006.01)

(52) U.S. Cl.
CPC ............. *C12N 15/67* (2013.01); *C12N 15/85* (2013.01); *C12N 2510/02* (2013.01)

(58) Field of Classification Search
None
See application file for complete search history.

(56) References Cited

U.S. PATENT DOCUMENTS

| | | | | |
|---|---|---|---|---|
| 5,122,469 A | * | 6/1992 | Mather | C12N 5/0037 435/383 |
| 6,040,149 A | * | 3/2000 | Kolesnick | C12N 9/1205 424/94.5 |
| 2014/0343167 A1 | * | 11/2014 | Chen | A61K 31/11 514/703 |

OTHER PUBLICATIONS

Sun et al article (PLOS One, pp. 1-9, published Aug. 11, 2009) (Year: 2009).*
Fischer et al "The art of CHO cell engineering: A comprehensive retrospect and future perspectives" (Biotechnology Advances vol. 33, available online Oct. 31, 2015; pp. 1878-1896). (Year: 2015).*
Bandaranayake & Almo "Recent Advances in Mammalian Protein Production" (FEBS Letters vol. 588, 2014, available online December (Year: 2014).*
No new reference cited (Year: 0000).*

* cited by examiner

*Primary Examiner* — Catherine S Hibbert
(74) *Attorney, Agent, or Firm* — Sheppars Mullin Richter & Hampton LLP

(57) ABSTRACT

The present disclosure relates to engineered cells that include genetic alterations leading to up- or down-regulation of certain genes in the cells for improved production of a recombinant protein. Also provided are methods of preparing and using such cells.

11 Claims, No Drawings

Specification includes a Sequence Listing.

ENGINEERED CELL LINES FOR INCREASED PROTEIN PRODUCTION

CROSS-REFERENCE TO RELATED APPLICATIONS

This application claims the benefit under of 35 U.S.C. § 119(e) of U.S. Provisional Application 62/255,306, filed on Nov. 13, 2015, the content of which is hereby incorporated by reference.

SEQUENCE LISTING

The instant application contains a Sequence Listing which has been filed electronically in ASCII format and is hereby incorporated by reference in its entirety. Said ASCII copy, created on Dec. 7, 2016, is named 45AH-221511-US_SL.txt and is 6,146 bytes in size.

BACKGROUND

Cell lines are frequently used for manufacturing protein therapeutic products. Among all commonly used lines, Chinese hamster ovary (CHO) cells remained as the preferred mammalian cell line for the production of recombinant protein therapeutic. Currently, recombinant protein titers from CHO cell culture have reached the gram per liter range which is a 100-fold improvement over similar process in the 1980s. The significant improvement of titer can be attributed to progress in establishment of stable and high producing clones as well as optimization of culture process.

To improve protein production, various cell line engineering strategies have been employed focusing on extending the longevity of cell culture, accelerating the specific growth rate and increasing the maximum viable cell density. Also, cell line engineering has been employed to improve the folding, transport and secretion of the recombinant protein. Despite these efforts, however, further improvement is needed for the overall efficiency of protein production.

SUMMARY

The present disclosure provides engineered cells that include genetic alterations leading to up- or down-regulation of certain genes in the cells for improved production of a recombinant protein. Also provided are methods of preparing and using such cells.

The experimental examples show that cell clones (e.g., clones 54 and 76) can have very different efficiency in protein expression while having similar genes introduced into the cells that are believed to be able to enhance protein expression. Closer examination showed that even though both clones 54 and 76 included recombinant Hk1 expression of Hk1 was about 6 times higher in clone 76 than in clone 54. It is contemplated that expression of Hk1 may not be high enough to make a difference in energy production in clone 54. In this context, the other growth enhancing genes (e.g., Akt1, Akt2, and 113) that are in common between the two clones had a bigger impact on the cells of clone 76 with higher energy production. Consistently, clone 73, which had a catabolic enhancement (e.g., Hk1) and a secondary enhancement (e.g., XIAP for enhancing cell survival), also had high titer.

It is believed, therefore, that enhancements to cell growth and protein production would have to be balanced out with enhanced energy production and nutrient metabolism. In this scenario, the starting enzyme in the glycolysis pathway, Hk1, which is a significant rate limiter in the pathway, worked in clone 76 to provide enough energy to the cells for enhancing growth rate while maintaining and even doubling titer.

It is also contemplated that enhancement of the catabolic pathway genes including any combination of the following genes: PDP, Hk1, pfk1, pkm, CS, and Idh3g, would have a synergistic effect on growth and protein expression when used in combination with genes intended to enhance protein folding, growth factors, anti-apoptosis, secretion, anabolics, gene expression (e.g., transcription initiation), and/or cytotoxicity. An example list of each category is described below.

| Pathway | Genes or supplements |
| --- | --- |
| Catabolism | Knockout or downregulate PDK1 and/or PDK4; upregulate PDP, Citrate Synthase, isocitrate dehydrogenase, PDH, DLAT, DLD, hexokinase (HK1), phosphofructokinase (pfk1), pyruvate kinase (pkm), and/or ATP synthase; supplement with ubiquinone and/or aspartic acid. |
| Protein folding | Upregulate Ero1la, XBP1S, PDI, Ero1lb, ERp57, GRP94, endoplasmin, calreticulin, PPI, alpha-lytic protease, subtilisin, Hsc/Hsp70, Hsp40, KAR2, GroEL, GroES, Hsp60, Cpn60, Dnak, DnaK cofactor (e.g., DnaJ, GrpE), Ssc1, Grp170, Hsp47, and/or ERp29. |
| Growth Factors | Upregulat Akt 1, Akt 2, Akt 3, IL3, p21, p27, MAPK1, and/or MAPK3; supplement with Rapamycin |
| Anti-apoptosis | Knockout or downregulate Caspase 8, Caspase 3, Caspase 9, Caspase 7, Caspase 6, and/or Fas-L; upregulate Gsk-3, Bcl-2, Bcl-xL, Aven, XIAP, Crma, and/or E1B-19k. |
| Secretion | Upregulate SRP14, Unc 18b, BiP, and/or Calnexin. |
| Anabolism | Upregulate Nrf2, HkII, Prdm1, Xbp1, IL2, IL5, PFKB2, AS160, and/or PIP5K. |
| Cytotoxicity | Knockout or downregulate LDHA; upregulate carbamoyl phosphate synthetase I, and/or transcarbamoylase. |
| Transcription Initiation | TBP |

Productivity of cells can be enhanced significantly by employing metabolic analysis through spent media analysis and media development. This could be an alternate method to control proper metabolite concentration in the cells for enhancing protein production, rather than relying on engineering the catabolic pathway. Spent media analysis and media supplementation may be used in addition to the method described above where engineering of anabolic pathway, secretion pathway, etc. was balanced with catabolic enhancements.

It is further contemplated that protein folding and secretion genes may have synergy with anabolic proteins. Overexpression of anabolic proteins would result in more energy expenditure on protein production. A rate limiting step in the process of protein production is the protein folding cycle, and potentially the protein secretion pathways as well. To ensure that there is no backlog in any point in the protein production pathways, resulting in misfolded and/or incomplete proteins, when overexpressing anabolic genes to enhance productivity, protein folding and secretory genes may have to be overexpressed as well.

Anti-apoptotic genes may have certain benefits such as longer cell viability, but may also have unintended disadvantages such as poor protein quality. As a cell enters the late stages of the cell cycle, toxic byproducts can build up in the cell, changing the pH of the cytoplasm causing misfolded, low quality proteins. These negative effects of extended cell life can potentially be mitigated through the co-overexpression of certain cytotoxicity management genes.

DETAILED DESCRIPTION

I. Definitions

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polynucleotide" includes a plurality of polynucleotides, including mixtures thereof.

The terms "polynucleotide" and "oligonucleotide" are used interchangeably and refer to a polymeric form of nucleotides of any length, either deoxyribonucleotides or ribonucleotides or analogs thereof. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

II. Cell Engineering

Metabolic pathways are broken up into catabolic and anabolic pathways. Catabolic pathways deal with turning glucose into ATP and anabolic pathways deal with turning glucose into proteins. There is an overlap of enzymes between these two pathways, while some steps are unique to each.

Cells generally control their own production of proteins and ATP, however through cellular engineering of the anabolic and catabolic pathways the cell machinery can be hijacked to produce more protein and the right type of protein. It is sometime not sufficient to regulate a single gene or pathway to achieve improved production of a protein.

The present disclosure provides genetically engineered cells that avoid the Warburg effect which is common to many protein production systems. The Warburg effect refers to cells drowning in ATP and other metabolites if there is an overabundance of these from overexpressing the genes for enhancing metabolites. For example, by replacing the natural (slow) glucose transporter with a rapid transporter, a cell of the present disclosure can control exactly how much glucose the cells consume by controlling the amount of glucose added. In another example, by increasing highly expressed gene transcript number, the cell will have enough target to put the metabolites into.

The genetic engineering employed in certain embodiments of the present disclosure helps to turn a cell into a factory, built mainly for growth and protein production. In some aspects, genetic alternations turn off some or all nonessential items for protein production or overexpress certain growth and production enzymes. In a preferred embodiment, both of these are implemented.

In some aspects, in order to not require too many genetic alternations but still achieving impact on a good number of genes, the genetic alternations can trigger cascades of excess production by overexpressing the rate limiting enzymes in a pathway. As such, by slightly increasing the effect of enough individual points along the pathway, the rate of the given pathway should increase. In this aspect, an engineered cell of the present disclosure can be viewed as a cell with distinct growth and production phases with each having regulatable control.

For instance, increasing the rate of the entire catabolic pathway results in an increase of byproduct metabolites which are necessary for efficiently creating proteins, so taking a holistic approach to catabolic engineering may pay off in anabolics as well.

Overall, the present disclosure identifies the main rate determining steps in the main pathways that turn glucose into ATP as well as other anabolic factors that can increase the rate of protein production, cell proliferation, and cell size.

Table 1 below lists a few genes that can be suitably targeted (for up- or down-regulation) for generating an engineered cell, as well as supply of nutritional factors in cell culture (Supply) for improved production of protein products.

TABLE 1

| No. | Gene(s)/Supplement(s) | Regulation | Function |
|---|---|---|---|
| | | Catabolics | |
| C1 | PDP | Up | rate control over ATP production through phosphorylation of the PDHc |
| C2 | CS and isocitrate dehydrogenase | Up | rate determining steps of the Kreb's Cycle |
| C3 | hk1, pfk1, or pkm | Up | Rate limiting steps of glucose oxidation into pyruvate |
| | | Anabolics | |
| A1 | Nrf2 | Up | Nrf2 redirects glucose and glutamine into anabolic pathways, especially under the sustained activation of PI3K-Akt signaling |
| A2 | Hk2 | Up | cytoplasmic HKII channel G-6-P towards regulating glycogen formation (anabolic use) |

TABLE 1-continued

| No. | Gene(s)/Supplement(s) | Regulation | Function |
|---|---|---|---|
| A3 | PFKB2, AS160, or PIP5K | Up | some of the various enzymes that are upregulated with Akt signaling, results in higher energy production and vesicle based transport |

Secretion

| No. | Gene(s)/Supplement(s) | Regulation | Function |
|---|---|---|---|
| S1 | Unc18b | Up | protein regulating the fusion of secretory vesicles to the plasma membrane |
| S2 | SRP14 | Up | CHO cells engineered to express SRP proteins such as SRP14 gained the ability to properly process and secrete the difficult-to-express immunoglobulin, and they also displayed improved secretion of an easy-to-express antibody. |
| S3 | BiP | Up | increases Igg solubility resulting in a 90% increase in secretion |
| S4 | Calnexin | Up | fends off ER stress induced apoptosis by ensuring proper protein folding |

Protein Folding

| No. | Gene(s)/Supplement(s) | Regulation | Function |
|---|---|---|---|
| F1 | XBP1S | Up | Regulator of protein folding and secretion, generally responsive to ER stress |

Growth Factors

| No. | Gene(s)/Supplement(s) | Regulation | Function |
|---|---|---|---|
| G1 | Akt1, Akt 2, or Akt 3 | Up | Akt pathways results in increased glucose uptake through increased glut1 expression, cell cycle progression, and cell survival pathways |
| G2 | p21, or p27 | Up | arrests the cell cycle at G1 allowing for more glucose to be channeled towards protein production |
| G3 | c-jun | Up | overexpression of c-Jun represses p53 and p21 expression and accelerates cell proliferation |

Cytotoxicity

| No. | Gene(s)/Supplement(s) | Regulation | Function |
|---|---|---|---|
| T1 | LDHA | Down | inhibit lactate production |
| T2 | carbamoyl phosphate synthetase I | Up | To reduce the level of the accumulated ammonium ion, carbamoyl phosphate synthetase I (CPS I) and ornithine transcarbamoylase (OTC) were used, which catalyze the first and second steps of the urea cycle in the liver. |
| T3 | transcarbamoylase | Up | To reduce the level of the accumulated ammonium ion, carbamoyl phosphate synthetase I (CPS I) and ornithine transcarbamoylase (OTC) were used, which catalyze the first and second steps of the urea cycle in the liver. |
| T4 | CAP | Up | transcription factor that regulates transcription of many catabolic operons involved in lactate metabolism |

Anti-Apoptosis

| No. | Gene(s)/Supplement(s) | Regulation | Function |
|---|---|---|---|
| P1 | Caspase 3 and/or 8 and/or 9 | Down | increase cell viability by knocking out cell death signaling proteins |
| P2 | Bcl2 or Bcl-xl | Up | antiapoptotic gene |
| P3 | XIAP | Up | XIAP is the most potent caspase inhibitor encoded in the mammalian genome. protein engineering of the XIAP protein can be used to alter the intracellular distribution pattern and improve the ability of this caspase inhibitor to protect against apoptosis for two mammalian cell lines. |

Gene Expression

| No. | Gene(s)/Supplement(s) | Regulation | Function |
|---|---|---|---|
| E1 | TBP | Up | first transcription factor in the transcription unit. Only TBP is necessary for transcription at promoters that contain a TATA box |
| E2 | Prdm1 or Blimp1 | Up | changes B-cells to resemble high producing plasma cells, this system may change the shape and function of CHO cells |
| E3 | IL3 | Up | activates various transcription factors such as JUN and FOS which are involved in the regulation of cell growth and differentiation. also inhibits apoptosis |

The following table (Table 2) lists additional genes in each category that can also be considered for targeted regulation when preparing an engineered cell of the present disclosure.

TABLE 2

| No. | Gene(s)/Supplement(s) | Regulation | Function |
|---|---|---|---|
| | | Catabolics | |
| C4 | PDK1 and/or PDK4 | Down | turns off the PDHc |
| C5 | PDH, DLAT, DLD | Up | turns pyruvate into acetyl coA |
| C6 | Ubiquinone | Supply | increase NADH production |
| C7 | Aspartatic Acid | Supply | increase cellular ability to manage electrons |
| C8 | ATP synthase subunits | Up | increase number of ATP synthases to increase ATP generation |
| | | Anabolics | |
| A4 | IL2 | Up | Involved in p13-Akt and TGF-beta pathways |
| A5 | IL5 | Up | Involved in p13-Akt and TGF-beta pathways |
| A6 | Glycogen Synthase | Up | Upregulated by the Akt pathway, converts glucose into glycogen sending the glucose to the protein production path |
| | | Protein Folding | |
| F2 | Ero1la | Up | Protein folding enzyme |
| F3 | PDI | Up | Protein folding enzyme |
| F4 | Ero1lb | Up | Protein folding enzyme |
| F5 | ERp57 | Up | ERp57 is a disulfide isomerase involved in the folding of a subset of glycoproteins in the ER as part of the calnexin/calreticulin cycle |
| F6 | GRP94 | Up | Embryonic stem (ES) cells that lack GRP94 are hypersensitive to stress conditions such as serum deprivation and die by apoptosis because they cannot respond to the stress by producing active IGF-II. This chaperone-client interaction may explain the previously documented antiapoptotic activity of GRP94 in a number of stress responses. |
| F7 | Endoplasmin | Up | a member of a family of adenosine triphosphate(ATP)-metabolizing molecular chaperones with roles in stabilizing and folding other proteins. The encoded protein is localized to melanosomes and the endoplasmic reticulum. |
| F8 | Calnexin | Up | also fends off ER stress induced apoptosis by ensuring proper protein folding |
| F9 | Calreticulin | Up | transcriptional regulation properties as well as calcium binding and protein folding |
| | | Growth Factors | |
| G4 | MAPK1 and/or MAPK3 | Up | Integration point for multiple biochemical signals, and are involved in a wide variety of cellular processes such as proliferation, differentiation, transcription regulation and development |
| G5 | Rapamycin | Supply | inhibits mTOR based autophagy |
| G6 | Smad2 and/or Smad3 | Up | The broad range of biological responses elicited by transforming growth factor-β (TGF-β) in various types of tissues and cells is mainly determined by the expression level and activity of the effector proteins Smad2 and Smad3. |
| | | Anti-Apoptosis | |
| P4 | Caspase 7 and/or 6 | Down | knockout of cell death signaling molecules extends viability of cells |
| P5 | Fas-1 | Down | Engagement of the cell death surface receptor Fas by Fas ligand (FasL) results in apoptotic cell death, mediated by caspase activation. |
| P6 | Gsk-3 | Up | Smad3 physically interacts with Axin and GSK3-β only in the absence of TGF-β. Reduction in the expression or activity of Axin/GSK3-β leads to increased Smad3 stability. The broad range of biological responses elicited by transforming growth factor-β (TGF-β) in various types of tissues |

TABLE 2-continued

| No. | Gene(s)/Supplement(s) | Regulation | Function |
|---|---|---|---|
| | | | and cells is mainly determined by the expression level and activity of the effector proteins Smad2 and Smad3. |
| P7 | Aven | Up | Aven appeared to act synergistically to enhance the protective function of Bcl-xL |
| P8 | Crma | Up | another caspase inhibitor, each inhibitor has varying degrees of effectiveness in different cases |
| P9 | E1b-19k | Up | The E1B 19K protein is a potent apoptosis inhibitor and the putative adenovirus Bcl-2 homolog. |
| | | Gene Expression | |
| E4 | Subunits of the TFIID complex | Up | TFIID is the transcription initiation complex, although TBP upregulation should be enough to affect the gene of interest, other individual subunits of the TFIID could similarly be upregulated to increase transcript initiation |
| E5 | Xbp1 | Up | activated by Blimp1 to increase gene expression |

In summary, the present disclosure contemplates genetic alternations resulting in up- or down-regulations (collectively "targeted modulation") of one or more genes as listed in Tables 1-2, which are summarized below. The up- or down-regulation is annotated in Tables 1-2 for each gene and is implied for the concerned gene throughout the disclosure.

| Category | Abbv | Primary | Secondary |
|---|---|---|---|
| Catabolics | C | C1-C3 | C4-C8 |
| Anabolics | A | A1-A3 | A4-A6 |
| Secretion | S | S1-S4 | |
| Protein Folding | F | F1 | F2-F9 |
| Growth Factors | G | G1-G3 | G4-G6 |
| Cytotoxicity | T | T1-T4 | |
| Anti-Apoptosis | P | P1-P3 | P4-P9 |
| Gene Expression | E | E1-E3 | E4-E5 |

Up- or down-regulation of a gene refers to a genetic or non-genetic change of the gene that leads to increased or decreased biological activity of the expression product (e.g., protein or RNA) in a cell. In one aspect, the regulation is at genetic level, such as mutation or deletion of either or both alleles of the gene. In one aspect, the regulation is at transcription level, e.g., through modulation of relevant transcription factors or elements, resulting in increased or decreased level of transcription. In one aspect, the regulation is at translation level, e.g., through codon optimization, leading to increased or decreased protein production. In one aspect, the regulation is at post-translational level, e.g., through post-translational modification. In one aspect, the regulation is at protein activity level, e.g., through generation of co-factors and inhibitors. In a preferred embodiment, down-regulation of a gene can be achieved by knocking out the gene (e.g., deletion of at least part of the gene). In a preferred embodiment, up-regulation of a gene can be achieved by duplicating the gene or replacing the promotor or another cis-transcription regulatory element with a stronger one.

In one embodiment, up- or down-regulation is as compared to a cell before the targeted modulation is made to the cell, such as an established cell line, a primary cell, or a cell that has been engineered otherwise.

In one embodiment, the engineered cell has targeted modulation of at least one gene of Table 1, or at least one gene of Table 2. In one embodiment, the engineered cell has targeted modulation of at least one gene in the catabolics category (e.g., C1-C8). In one embodiment, the engineered cell has targeted modulation of at least one gene in the anabolics category (e.g., A1-A6). In one embodiment, the engineered cell has targeted modulation of at least one gene in the secretion category (e.g., S1-S4). In one embodiment, the engineered cell has targeted modulation of at least one gene in the protein folding category (e.g., F1-F9). In one embodiment, the engineered cell has targeted modulation of at least one gene in the growth factors category (e.g., G1-G6). In one embodiment, the engineered cell has targeted modulation of at least one gene in the cytotoxicity category (e.g., T1-T4). In one embodiment, the engineered cell has targeted modulation of at least one gene in the anti-apoptosis category (e.g., P1-P9). In one embodiment, the engineered cell has targeted modulation of at least one gene in the gene expression category (e.g., E1-E5).

In one embodiment, the engineered cell has targeted modulation of at least one gene from a first category and another gene from a second category, as illustrated below. In one embodiment, the engineered cell further has targeted modulation of at least one gene from a third category, also illustrated below. In one aspect, each of the genes is selected from Table 1 only. In one aspect, the genes can be selected from Table 1 or Table 2.

| First category | Second category | Third category |
|---|---|---|
| Catabolics | Anabolics | Catabolics, Anabolics, Secretion, Protein Folding, Growth Factors, Cytotoxicity, Anti-Apoptosis, or Gene Expression |
| Catabolics | Secretion | Catabolics, Anabolics, Secretion, Protein Folding, Growth Factors, Cytotoxicity, Anti-Apoptosis, or Gene Expression |
| Catabolics | Protein Folding | Catabolics, Anabolics, Secretion, Protein Folding, Growth Factors, Cytotoxicity, Anti-Apoptosis, or Gene Expression |

-continued

| First category | Second category | Third category |
| --- | --- | --- |
| Catabolics | Growth Factors | Catabolics, Anabolics, Secretion, Protein Folding, Growth Factors, Cytotoxicity, Anti-Apoptosis, or Gene Expression |
| Catabolics | Cytotoxicity | Catabolics, Anabolics, Secretion, Protein Folding, Growth Factors, Cytotoxicity, Anti-Apoptosis, or Gene Expression |
| Catabolics | Anti-Apoptosis | Catabolics, Anabolics, Secretion, Protein Folding, Growth Factors, Cytotoxicity, Anti-Apoptosis, or Gene Expression |
| Catabolics | Gene Expression | Catabolics, Anabolics, Secretion, Protein Folding, Growth Factors, Cytotoxicity, Anti-Apoptosis, or Gene Expression |
| Anabolics | Catabolics | Catabolics, Anabolics, Secretion, Protein Folding, Growth Factors, Cytotoxicity, Anti-Apoptosis, or Gene Expression |
| Anabolics | Secretion | Catabolics, Anabolics, Secretion, Protein Folding, Growth Factors, Cytotoxicity, Anti-Apoptosis, or Gene Expression |
| Anabolics | Protein Folding | Catabolics, Anabolics, Secretion, Protein Folding, Growth Factors, Cytotoxicity, Anti-Apoptosis, or Gene Expression |
| Anabolics | Growth Factors | Catabolics, Anabolics, Secretion, Protein Folding, Growth Factors, Cytotoxicity, Anti-Apoptosis, or Gene Expression |
| Anabolics | Cytotoxicity | Catabolics, Anabolics, Secretion, Protein Folding, Growth Factors, Cytotoxicity, Anti-Apoptosis, or Gene Expression |
| Anabolics | Anti-Apoptosis | Catabolics, Anabolics, Secretion, Protein Folding, Growth Factors, Cytotoxicity, Anti-Apoptosis, or Gene Expression |
| Anabolics | Gene Expression | Catabolics, Anabolics, Secretion, Protein Folding, Growth Factors, Cytotoxicity, Anti-Apoptosis, or Gene Expression |
| Secretion | Catabolics | Catabolics, Anabolics, Secretion, Protein Folding, Growth Factors, Cytotoxicity, Anti-Apoptosis, or Gene Expression |
| Secretion | Anabolics | Catabolics, Anabolics, Secretion, Protein Folding, Growth Factors, Cytotoxicity, Anti-Apoptosis, or Gene Expression |
| Secretion | Protein Folding | Catabolics, Anabolics, Secretion, Protein Folding, Growth Factors, Cytotoxicity, Anti-Apoptosis, or Gene Expression |
| Secretion | Growth Factors | Catabolics, Anabolics, Secretion, Protein Folding, Growth Factors, Cytotoxicity, Anti-Apoptosis, or Gene Expression |
| Secretion | Cytotoxicity | Catabolics, Anabolics, Secretion, Protein Folding, Growth Factors, Cytotoxicity, Anti-Apoptosis, or Gene Expression |
| Secretion | Anti-Apoptosis | Catabolics, Anabolics, Secretion, Protein Folding, Growth Factors, Cytotoxicity, Anti-Apoptosis, or Gene Expression |
| Secretion | Gene Expression | Catabolics, Anabolics, Secretion, Protein Folding, Growth Factors, Cytotoxicity, Anti-Apoptosis, or Gene Expression |
| Protein Folding | Catabolics | Catabolics, Anabolics, Secretion, Protein Folding, Growth Factors, Cytotoxicity, Anti-Apoptosis, or Gene Expression |
| Protein Folding | Anabolics | Catabolics, Anabolics, Secretion, Protein Folding, Growth Factors, Cytotoxicity, Anti-Apoptosis, or Gene Expression |
| Protein Folding | Secretion | Catabolics, Anabolics, Secretion, Protein Folding, Growth Factors, Cytotoxicity, Anti-Apoptosis, or Gene Expression |
| Protein Folding | Growth Factors | Catabolics, Anabolics, Secretion, Protein Folding, Growth Factors, Cytotoxicity, Anti-Apoptosis, or Gene Expression |
| Protein Folding | Cytotoxicity | Catabolics, Anabolics, Secretion, Protein Folding, Growth Factors, Cytotoxicity, Anti-Apoptosis, or Gene Expression |
| Protein Folding | Anti-Apoptosis | Catabolics, Anabolics, Secretion, Protein Folding, Growth Factors, Cytotoxicity, Anti-Apoptosis, or Gene Expression |
| Protein Folding | Gene Expression | Catabolics, Anabolics, Secretion, Protein Folding, Growth Factors, Cytotoxicity, Anti-Apoptosis, or Gene Expression |
| Growth Factors | Catabolics | Catabolics, Anabolics, Secretion, Protein Folding, Growth Factors, Cytotoxicity, Anti-Apoptosis, or Gene Expression |
| Growth Factors | Anabolics | Catabolics, Anabolics, Secretion, Protein Folding, Growth Factors, Cytotoxicity, Anti-Apoptosis, or Gene Expression |
| Growth Factors | Secretion | Catabolics, Anabolics, Secretion, Protein Folding, Growth Factors, Cytotoxicity, Anti-Apoptosis, or Gene Expression |
| Growth Factors | Protein Folding | Catabolics, Anabolics, Secretion, Protein Folding, Growth Factors, Cytotoxicity, Anti-Apoptosis, or Gene Expression |
| Growth Factors | Cytotoxicity | Catabolics, Anabolics, Secretion, Protein Folding, Growth Factors, Cytotoxicity, Anti-Apoptosis, or Gene Expression |
| Growth Factors | Anti-Apoptosis | Catabolics, Anabolics, Secretion, Protein Folding, Growth Factors, Cytotoxicity, Anti-Apoptosis, or Gene Expression |
| Growth Factors | Gene Expression | Catabolics, Anabolics, Secretion, Protein Folding, Growth Factors, Cytotoxicity, Anti-Apoptosis, or Gene Expression |
| Cytotoxicity | Catabolics | Catabolics, Anabolics, Secretion, Protein Folding, Growth Factors, Cytotoxicity, Anti-Apoptosis, or Gene Expression |
| Cytotoxicity | Anabolics | Catabolics, Anabolics, Secretion, Protein Folding, Growth Factors, Cytotoxicity, Anti-Apoptosis, or Gene Expression |
| Cytotoxicity | Secretion | Catabolics, Anabolics, Secretion, Protein Folding, Growth Factors, Cytotoxicity, Anti-Apoptosis, or Gene Expression |
| Cytotoxicity | Protein Folding | Catabolics, Anabolics, Secretion, Protein Folding, Growth Factors, Cytotoxicity, Anti-Apoptosis, or Gene Expression |
| Cytotoxicity | Growth Factors | Catabolics, Anabolics, Secretion, Protein Folding, Growth Factors, Cytotoxicity, Anti-Apoptosis, or Gene Expression |
| Cytotoxicity | Anti-Apoptosis | Catabolics, Anabolics, Secretion, Protein Folding, Growth Factors, Cytotoxicity, Anti-Apoptosis, or Gene Expression |

-continued

| First category | Second category | Third category |
|---|---|---|
| Cytotoxicity | Gene Expression | Catabolics, Anabolics, Secretion, Protein Folding, Growth Factors, Cytotoxicity, Anti-Apoptosis, or Gene Expression |
| Anti-Apoptosis | Catabolics | Catabolics, Anabolics, Secretion, Protein Folding, Growth Factors, Cytotoxicity, Anti-Apoptosis, or Gene Expression |
| Anti-Apoptosis | Anabolics | Catabolics, Anabolics, Secretion, Protein Folding, Growth Factors, Cytotoxicity, Anti-Apoptosis, or Gene Expression |
| Anti-Apoptosis | Secretion | Catabolics, Anabolics, Secretion, Protein Folding, Growth Factors, Cytotoxicity, Anti-Apoptosis, or Gene Expression |
| Anti-Apoptosis | Protein Folding | Catabolics, Anabolics, Secretion, Protein Folding, Growth Factors, Cytotoxicity, Anti-Apoptosis, or Gene Expression |
| Anti-Apoptosis | Growth Factors | Catabolics, Anabolics, Secretion, Protein Folding, Growth Factors, Cytotoxicity, Anti-Apoptosis, or Gene Expression |
| Anti-Apoptosis | Cytotoxicity | Catabolics, Anabolics, Secretion, Protein Folding, Growth Factors, Cytotoxicity, Anti-Apoptosis, or Gene Expression |
| Anti-Apoptosis | Gene Expression | Catabolics, Anabolics, Secretion, Protein Folding, Growth Factors, Cytotoxicity, Anti-Apoptosis, or Gene Expression |
| Gene Expression | Catabolics | Catabolics, Anabolics, Secretion, Protein Folding, Growth Factors, Cytotoxicity, Anti-Apoptosis, or Gene Expression |
| Gene Expression | Anabolics | Catabolics, Anabolics, Secretion, Protein Folding, Growth Factors, Cytotoxicity, Anti-Apoptosis, or Gene Expression |
| Gene Expression | Secretion | Catabolics, Anabolics, Secretion, Protein Folding, Growth Factors, Cytotoxicity, Anti-Apoptosis, or Gene Expression |
| Gene Expression | Protein Folding | Catabolics, Anabolics, Secretion, Protein Folding, Growth Factors, Cytotoxicity, Anti-Apoptosis, or Gene Expression |
| Gene Expression | Growth Factors | Catabolics, Anabolics, Secretion, Protein Folding, Growth Factors, Cytotoxicity, Anti-Apoptosis, or Gene Expression |
| Gene Expression | Cytotoxicity | Catabolics, Anabolics, Secretion, Protein Folding, Growth Factors, Cytotoxicity, Anti-Apoptosis, or Gene Expression |
| Gene Expression | Anti-Apoptosis | Catabolics, Anabolics, Secretion, Protein Folding, Growth Factors, Cytotoxicity, Anti-Apoptosis, or Gene Expression |

In one aspect, the engineered cell has targeted modulation of at least two genes, as indicated by any of the X's in the following table (Table 3) (row headers: gene one; column header: gene two).

TABLE 3

|    | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
|---|---|---|---|---|---|---|---|---|---|---|---|---|---|---|---|---|---|---|---|---|---|---|---|---|
| C1 |   |   |   |   |   |   |   |   |   |   |   |   |   |   |   |   |   |   |   |   |   |   |   |   |
| C2 | X |   |   |   |   |   |   |   |   |   |   |   |   |   |   |   |   |   |   |   |   |   |   |   |
| C3 | X | X |   |   |   |   |   |   |   |   |   |   |   |   |   |   |   |   |   |   |   |   |   |   |
| A1 | X | X | X |   |   |   |   |   |   |   |   |   |   |   |   |   |   |   |   |   |   |   |   |   |
| A2 | X | X | X | X |   |   |   |   |   |   |   |   |   |   |   |   |   |   |   |   |   |   |   |   |
| A3 | X | X | X | X | X |   |   |   |   |   |   |   |   |   |   |   |   |   |   |   |   |   |   |   |
| S1 | X | X | X | X | X | X |   |   |   |   |   |   |   |   |   |   |   |   |   |   |   |   |   |   |
| S2 | X | X | X | X | X | X | X |   |   |   |   |   |   |   |   |   |   |   |   |   |   |   |   |   |
| S3 | X | X | X | X | X | X | X | X |   |   |   |   |   |   |   |   |   |   |   |   |   |   |   |   |
| S4 | X | X | X | X | X | X | X | X | X |   |   |   |   |   |   |   |   |   |   |   |   |   |   |   |
| F1 | X | X | X | X | X | X | X | X | X | X |   |   |   |   |   |   |   |   |   |   |   |   |   |   |
| G1 | X | X | X | X | X | X | X | X | X | X | X |   |   |   |   |   |   |   |   |   |   |   |   |   |
| G2 | X | X | X | X | X | X | X | X | X | X | X | X |   |   |   |   |   |   |   |   |   |   |   |   |
| G3 | X | X | X | X | X | X | X | X | X | X | X | X | X |   |   |   |   |   |   |   |   |   |   |   |
| T1 | X | X | X | X | X | X | X | X | X | X | X | X | X | X |   |   |   |   |   |   |   |   |   |   |
| T2 | X | X | X | X | X | X | X | X | X | X | X | X | X | X | X |   |   |   |   |   |   |   |   |   |
| T3 | X | X | X | X | X | X | X | X | X | X | X | X | X | X | X | X |   |   |   |   |   |   |   |   |
| T4 | X | X | X | X | X | X | X | X | X | X | X | X | X | X | X | X | X |   |   |   |   |   |   |   |
| P1 | X | X | X | X | X | X | X | X | X | X | X | X | X | X | X | X | X | X |   |   |   |   |   |   |
| P2 | X | X | X | X | X | X | X | X | X | X | X | X | X | X | X | X | X | X | X |   |   |   |   |   |
| P3 | X | X | X | X | X | X | X | X | X | X | X | X | X | X | X | X | X | X | X | X |   |   |   |   |
| E1 | X | X | X | X | X | X | X | X | X | X | X | X | X | X | X | X | X | X | X | X | X |   |   |   |
| E2 | X | X | X | X | X | X | X | X | X | X | X | X | X | X | X | X | X | X | X | X | X | X |   |   |
| E3 | X | X | X | X | X | X | X | X | X | X | X | X | X | X | X | X | X | X | X | X | X | X | X |   |

In one aspect, the engineered cell has targeted modulation of at least three genes, as indicated by any of the X's in the following table (Table 4) (columns 1 and 2 for each row: genes 1 and 2; other column heads: gene 3).

TABLE 4

| Gene 1 | Gene 2 | Gene 3 | | | | | | | | | | | | | | | | | | | | | |
|---|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| C1 | C2 | X | X | X | X | X | X | X | X | X | X | X | X | X | X | X | X | X | X | X | X | X | X | X | X |
| C1 | C3 | X | X | X | X | X | X | X | X | X | X | X | X | X | X | X | X | X | X | X | X | X | X | X | X |
| C1 | A1 | X | X | X | X | X | X | X | X | X | X | X | X | X | X | X | X | X | X | X | X | X | X | X | X |
| C1 | A2 | X | X | X | X | X | X | X | X | X | X | X | X | X | X | X | X | X | X | X | X | X | X | X | X |
| C1 | A3 | X | X | X | X | X | X | X | X | X | X | X | X | X | X | X | X | X | X | X | X | X | X | X | X |
| C1 | S1 | X | X | X | X | X | X | X | X | X | X | X | X | X | X | X | X | X | X | X | X | X | X | X | X |
| C1 | S2 | X | X | X | X | X | X | X | X | X | X | X | X | X | X | X | X | X | X | X | X | X | X | X | X |
| C1 | S3 | X | X | X | X | X | X | X | X | X | X | X | X | X | X | X | X | X | X | X | X | X | X | X | X |
| C1 | S4 | X | X | X | X | X | X | X | X | X | X | X | X | X | X | X | X | X | X | X | X | X | X | X | X |
| C1 | F1 | X | X | X | X | X | X | X | X | X | X | X | X | X | X | X | X | X | X | X | X | X | X | X | X |
| C1 | G1 | X | X | X | X | X | X | X | X | X | X | X | X | X | X | X | X | X | X | X | X | X | X | X | X |
| C1 | G2 | X | X | X | X | X | X | X | X | X | X | X | X | X | X | X | X | X | X | X | X | X | X | X | X |
| C1 | G3 | X | X | X | X | X | X | X | X | X | X | X | X | X | X | X | X | X | X | X | X | X | X | X | X |
| C1 | T1 | X | X | X | X | X | X | X | X | X | X | X | X | X | X | X | X | X | X | X | X | X | X | X | X |
| C1 | T2 | X | X | X | X | X | X | X | X | X | X | X | X | X | X | X | X | X | X | X | X | X | X | X | X |
| C1 | T3 | X | X | X | X | X | X | X | X | X | X | X | X | X | X | X | X | X | X | X | X | X | X | X | X |
| C1 | T4 | X | X | X | X | X | X | X | X | X | X | X | X | X | X | X | X | X | X | X | X | X | X | X | X |
| C1 | P1 | X | X | X | X | X | X | X | X | X | X | X | X | X | X | X | X | X | X | X | X | X | X | X | X |
| C1 | P2 | X | X | X | X | X | X | X | X | X | X | X | X | X | X | X | X | X | X | X | X | X | X | X | X |
| C1 | P3 | X | X | X | X | X | X | X | X | X | X | X | X | X | X | X | X | X | X | X | X | X | X | X | X |
| C1 | E1 | X | X | X | X | X | X | X | X | X | X | X | X | X | X | X | X | X | X | X | X | X | X | X | X |
| C1 | E2 | X | X | X | X | X | X | X | X | X | X | X | X | X | X | X | X | X | X | X | X | X | X | X | X |
| C1 | E3 | X | X | X | X | X | X | X | X | X | X | X | X | X | X | X | X | X | X | X | X | X | X | X | X |
| C2 | C1 | X | X | X | X | X | X | X | X | X | X | X | X | X | X | X | X | X | X | X | X | X | X | X | X |
| C2 | C3 | X | X | X | X | X | X | X | X | X | X | X | X | X | X | X | X | X | X | X | X | X | X | X | X |
| C2 | A1 | X | X | X | X | X | X | X | X | X | X | X | X | X | X | X | X | X | X | X | X | X | X | X | X |
| C2 | A2 | X | X | X | X | X | X | X | X | X | X | X | X | X | X | X | X | X | X | X | X | X | X | X | X |
| C2 | A3 | X | X | X | X | X | X | X | X | X | X | X | X | X | X | X | X | X | X | X | X | X | X | X | X |
| C2 | S1 | X | X | X | X | X | X | X | X | X | X | X | X | X | X | X | X | X | X | X | X | X | X | X | X |
| C2 | S2 | X | X | X | X | X | X | X | X | X | X | X | X | X | X | X | X | X | X | X | X | X | X | X | X |
| C2 | S3 | X | X | X | X | X | X | X | X | X | X | X | X | X | X | X | X | X | X | X | X | X | X | X | X |
| C2 | S4 | X | X | X | X | X | X | X | X | X | X | X | X | X | X | X | X | X | X | X | X | X | X | X | X |
| C2 | F1 | X | X | X | X | X | X | X | X | X | X | X | X | X | X | X | X | X | X | X | X | X | X | X | X |
| C2 | G1 | X | X | X | X | X | X | X | X | X | X | X | X | X | X | X | X | X | X | X | X | X | X | X | X |
| C2 | G2 | X | X | X | X | X | X | X | X | X | X | X | X | X | X | X | X | X | X | X | X | X | X | X | X |
| C2 | G3 | X | X | X | X | X | X | X | X | X | X | X | X | X | X | X | X | X | X | X | X | X | X | X | X |
| C2 | T1 | X | X | X | X | X | X | X | X | X | X | X | X | X | X | X | X | X | X | X | X | X | X | X | X |
| C2 | T2 | X | X | X | X | X | X | X | X | X | X | X | X | X | X | X | X | X | X | X | X | X | X | X | X |
| C2 | T3 | X | X | X | X | X | X | X | X | X | X | X | X | X | X | X | X | X | X | X | X | X | X | X | X |
| C2 | T4 | X | X | X | X | X | X | X | X | X | X | X | X | X | X | X | X | X | X | X | X | X | X | X | X |
| C2 | P1 | X | X | X | X | X | X | X | X | X | X | X | X | X | X | X | X | X | X | X | X | X | X | X | X |
| C2 | P2 | X | X | X | X | X | X | X | X | X | X | X | X | X | X | X | X | X | X | X | X | X | X | X | X |
| C2 | P3 | X | X | X | X | X | X | X | X | X | X | X | X | X | X | X | X | X | X | X | X | X | X | X | X |
| C2 | E1 | X | X | X | X | X | X | X | X | X | X | X | X | X | X | X | X | X | X | X | X | X | X | X | X |
| C2 | E2 | X | X | X | X | X | X | X | X | X | X | X | X | X | X | X | X | X | X | X | X | X | X | X | X |
| C2 | E3 | X | X | X | X | X | X | X | X | X | X | X | X | X | X | X | X | X | X | X | X | X | X | X | X |
| C3 | C1 | X | X | X | X | X | X | X | X | X | X | X | X | X | X | X | X | X | X | X | X | X | X | X | X |
| C3 | C2 | X | X | X | X | X | X | X | X | X | X | X | X | X | X | X | X | X | X | X | X | X | X | X | X |
| C3 | A1 | X | X | X | X | X | X | X | X | X | X | X | X | X | X | X | X | X | X | X | X | X | X | X | X |
| C3 | A2 | X | X | X | X | X | X | X | X | X | X | X | X | X | X | X | X | X | X | X | X | X | X | X | X |
| C3 | A3 | X | X | X | X | X | X | X | X | X | X | X | X | X | X | X | X | X | X | X | X | X | X | X | X |
| C3 | S1 | X | X | X | X | X | X | X | X | X | X | X | X | X | X | X | X | X | X | X | X | X | X | X | X |
| C3 | S2 | X | X | X | X | X | X | X | X | X | X | X | X | X | X | X | X | X | X | X | X | X | X | X | X |
| C3 | S3 | X | X | X | X | X | X | X | X | X | X | X | X | X | X | X | X | X | X | X | X | X | X | X | X |
| C3 | S4 | X | X | X | X | X | X | X | X | X | X | X | X | X | X | X | X | X | X | X | X | X | X | X | X |
| C3 | F1 | X | X | X | X | X | X | X | X | X | X | X | X | X | X | X | X | X | X | X | X | X | X | X | X |
| C3 | G1 | X | X | X | X | X | X | X | X | X | X | X | X | X | X | X | X | X | X | X | X | X | X | X | X |
| C3 | G2 | X | X | X | X | X | X | X | X | X | X | X | X | X | X | X | X | X | X | X | X | X | X | X | X |
| C3 | G3 | X | X | X | X | X | X | X | X | X | X | X | X | X | X | X | X | X | X | X | X | X | X | X | X |
| C3 | T1 | X | X | X | X | X | X | X | X | X | X | X | X | X | X | X | X | X | X | X | X | X | X | X | X |
| C3 | T2 | X | X | X | X | X | X | X | X | X | X | X | X | X | X | X | X | X | X | X | X | X | X | X | X |
| C3 | T3 | X | X | X | X | X | X | X | X | X | X | X | X | X | X | X | X | X | X | X | X | X | X | X | X |
| C3 | T4 | X | X | X | X | X | X | X | X | X | X | X | X | X | X | X | X | X | X | X | X | X | X | X | X |
| C3 | P1 | X | X | X | X | X | X | X | X | X | X | X | X | X | X | X | X | X | X | X | X | X | X | X | X |
| C3 | P2 | X | X | X | X | X | X | X | X | X | X | X | X | X | X | X | X | X | X | X | X | X | X | X | X |
| C3 | P3 | X | X | X | X | X | X | X | X | X | X | X | X | X | X | X | X | X | X | X | X | X | X | X | X |
| C3 | E1 | X | X | X | X | X | X | X | X | X | X | X | X | X | X | X | X | X | X | X | X | X | X | X | X |
| C3 | E2 | X | X | X | X | X | X | X | X | X | X | X | X | X | X | X | X | X | X | X | X | X | X | X | X |
| C3 | E3 | X | X | X | X | X | X | X | X | X | X | X | X | X | X | X | X | X | X | X | X | X | X | X | X |
| A1 | C1 | X | X | X | X | X | X | X | X | X | X | X | X | X | X | X | X | X | X | X | X | X | X | X | X |
| A1 | C2 | X | X | X | X | X | X | X | X | X | X | X | X | X | X | X | X | X | X | X | X | X | X | X | X |
| A1 | C3 | X | X | X | X | X | X | X | X | X | X | X | X | X | X | X | X | X | X | X | X | X | X | X | X |
| A1 | A2 | X | X | X | X | X | X | X | X | X | X | X | X | X | X | X | X | X | X | X | X | X | X | X | X |
| A1 | A3 | X | X | X | X | X | X | X | X | X | X | X | X | X | X | X | X | X | X | X | X | X | X | X | X |
| A1 | S1 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | |
|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| A1 | S2 | X | X | X | X | X | X | X | X | X | X | X | X | X | X | X | X | X | X | X | X | X | X | X | X |
| A1 | S3 | X | X | X | X | X | X | X | X | X | X | X | X | X | X | X | X | X | X | X | X | X | X | X | X |
| A1 | S4 | X | X | X | X | X | X | X | X | X | X | X | X | X | X | X | X | X | X | X | X | X | X | X | X |
| A1 | F1 | X | X | X | X | X | X | X | X | X | X | X | X | X | X | X | X | X | X | X | X | X | X | X | X |
| A1 | G1 | X | X | X | X | X | X | X | X | X | X | X | X | X | X | X | X | X | X | X | X | X | X | X | X |
| A1 | G2 | X | X | X | X | X | X | X | X | X | X | X | X | X | X | X | X | X | X | X | X | X | X | X | X |
| A1 | G3 | X | X | X | X | X | X | X | X | X | X | X | X | X | X | X | X | X | X | X | X | X | X | X | X |
| A1 | T1 | X | X | X | X | X | X | X | X | X | X | X | X | X | X | X | X | X | X | X | X | X | X | X | X |
| A1 | T2 | X | X | X | X | X | X | X | X | X | X | X | X | X | X | X | X | X | X | X | X | X | X | X | X |
| A1 | T3 | X | X | X | X | X | X | X | X | X | X | X | X | X | X | X | X | X | X | X | X | X | X | X | X |
| A1 | T4 | X | X | X | X | X | X | X | X | X | X | X | X | X | X | X | X | X | X | X | X | X | X | X | X |
| A1 | P1 | X | X | X | X | X | X | X | X | X | X | X | X | X | X | X | X | X | X | X | X | X | X | X | X |
| A1 | P2 | X | X | X | X | X | X | X | X | X | X | X | X | X | X | X | X | X | X | X | X | X | X | X | X |
| A1 | P3 | X | X | X | X | X | X | X | X | X | X | X | X | X | X | X | X | X | X | X | X | X | X | X | X |
| A1 | E1 | X | X | X | X | X | X | X | X | X | X | X | X | X | X | X | X | X | X | X | X | X | X | X | X |
| A1 | E2 | X | X | X | X | X | X | X | X | X | X | X | X | X | X | X | X | X | X | X | X | X | X | X | X |
| A1 | E3 | X | X | X | X | X | X | X | X | X | X | X | X | X | X | X | X | X | X | X | X | X | X | X | X |
| A2 | C1 | X | X | X | X | X | X | X | X | X | X | X | X | X | X | X | X | X | X | X | X | X | X | X | X |
| A2 | C2 | X | X | X | X | X | X | X | X | X | X | X | X | X | X | X | X | X | X | X | X | X | X | X | X |
| A2 | C3 | X | X | X | X | X | X | X | X | X | X | X | X | X | X | X | X | X | X | X | X | X | X | X | X |
| A2 | A1 | X | X | X | X | X | X | X | X | X | X | X | X | X | X | X | X | X | X | X | X | X | X | X | X |
| A2 | A3 | X | X | X | X | X | X | X | X | X | X | X | X | X | X | X | X | X | X | X | X | X | X | X | X |
| A2 | S1 | X | X | X | X | X | X | X | X | X | X | X | X | X | X | X | X | X | X | X | X | X | X | X | X |
| A2 | S2 | X | X | X | X | X | X | X | X | X | X | X | X | X | X | X | X | X | X | X | X | X | X | X | X |
| A2 | S3 | X | X | X | X | X | X | X | X | X | X | X | X | X | X | X | X | X | X | X | X | X | X | X | X |
| A2 | S4 | X | X | X | X | X | X | X | X | X | X | X | X | X | X | X | X | X | X | X | X | X | X | X | X |
| A2 | F1 | X | X | X | X | X | X | X | X | X | X | X | X | X | X | X | X | X | X | X | X | X | X | X | X |
| A2 | G1 | X | X | X | X | X | X | X | X | X | X | X | X | X | X | X | X | X | X | X | X | X | X | X | X |
| A2 | G2 | X | X | X | X | X | X | X | X | X | X | X | X | X | X | X | X | X | X | X | X | X | X | X | X |
| A2 | G3 | X | X | X | X | X | X | X | X | X | X | X | X | X | X | X | X | X | X | X | X | X | X | X | X |
| A2 | T1 | X | X | X | X | X | X | X | X | X | X | X | X | X | X | X | X | X | X | X | X | X | X | X | X |
| A2 | T2 | X | X | X | X | X | X | X | X | X | X | X | X | X | X | X | X | X | X | X | X | X | X | X | X |
| A2 | T3 | X | X | X | X | X | X | X | X | X | X | X | X | X | X | X | X | X | X | X | X | X | X | X | X |
| A2 | T4 | X | X | X | X | X | X | X | X | X | X | X | X | X | X | X | X | X | X | X | X | X | X | X | X |
| A2 | P1 | X | X | X | X | X | X | X | X | X | X | X | X | X | X | X | X | X | X | X | X | X | X | X | X |
| A2 | P2 | X | X | X | X | X | X | X | X | X | X | X | X | X | X | X | X | X | X | X | X | X | X | X | X |
| A2 | P3 | X | X | X | X | X | X | X | X | X | X | X | X | X | X | X | X | X | X | X | X | X | X | X | X |
| A2 | E1 | X | X | X | X | X | X | X | X | X | X | X | X | X | X | X | X | X | X | X | X | X | X | X | X |
| A2 | E2 | X | X | X | X | X | X | X | X | X | X | X | X | X | X | X | X | X | X | X | X | X | X | X | X |
| A2 | E3 | X | X | X | X | X | X | X | X | X | X | X | X | X | X | X | X | X | X | X | X | X | X | X | X |
| A3 | C1 | X | X | X | X | X | X | X | X | X | X | X | X | X | X | X | X | X | X | X | X | X | X | X | X |
| A3 | C2 | X | X | X | X | X | X | X | X | X | X | X | X | X | X | X | X | X | X | X | X | X | X | X | X |
| A3 | C3 | X | X | X | X | X | X | X | X | X | X | X | X | X | X | X | X | X | X | X | X | X | X | X | X |
| A3 | A1 | X | X | X | X | X | X | X | X | X | X | X | X | X | X | X | X | X | X | X | X | X | X | X | X |
| A3 | A2 | X | X | X | X | X | X | X | X | X | X | X | X | X | X | X | X | X | X | X | X | X | X | X | X |
| A3 | S1 | X | X | X | X | X | X | X | X | X | X | X | X | X | X | X | X | X | X | X | X | X | X | X | X |
| A3 | S2 | X | X | X | X | X | X | X | X | X | X | X | X | X | X | X | X | X | X | X | X | X | X | X | X |
| A3 | S3 | X | X | X | X | X | X | X | X | X | X | X | X | X | X | X | X | X | X | X | X | X | X | X | X |
| A3 | S4 | X | X | X | X | X | X | X | X | X | X | X | X | X | X | X | X | X | X | X | X | X | X | X | X |
| A3 | F1 | X | X | X | X | X | X | X | X | X | X | X | X | X | X | X | X | X | X | X | X | X | X | X | X |
| A3 | G1 | X | X | X | X | X | X | X | X | X | X | X | X | X | X | X | X | X | X | X | X | X | X | X | X |
| A3 | G2 | X | X | X | X | X | X | X | X | X | X | X | X | X | X | X | X | X | X | X | X | X | X | X | X |
| A3 | G3 | X | X | X | X | X | X | X | X | X | X | X | X | X | X | X | X | X | X | X | X | X | X | X | X |
| A3 | T1 | X | X | X | X | X | X | X | X | X | X | X | X | X | X | X | X | X | X | X | X | X | X | X | X |
| A3 | T2 | X | X | X | X | X | X | X | X | X | X | X | X | X | X | X | X | X | X | X | X | X | X | X | X |
| A3 | T3 | X | X | X | X | X | X | X | X | X | X | X | X | X | X | X | X | X | X | X | X | X | X | X | X |
| A3 | T4 | X | X | X | X | X | X | X | X | X | X | X | X | X | X | X | X | X | X | X | X | X | X | X | X |
| A3 | P1 | X | X | X | X | X | X | X | X | X | X | X | X | X | X | X | X | X | X | X | X | X | X | X | X |
| A3 | P2 | X | X | X | X | X | X | X | X | X | X | X | X | X | X | X | X | X | X | X | X | X | X | X | X |
| A3 | P3 | X | X | X | X | X | X | X | X | X | X | X | X | X | X | X | X | X | X | X | X | X | X | X | X |
| A3 | E1 | X | X | X | X | X | X | X | X | X | X | X | X | X | X | X | X | X | X | X | X | X | X | X | X |
| A3 | E2 | X | X | X | X | X | X | X | X | X | X | X | X | X | X | X | X | X | X | X | X | X | X | X | X |
| A3 | E3 | X | X | X | X | X | X | X | X | X | X | X | X | X | X | X | X | X | X | X | X | X | X | X | X |
| S1 | C1 | X | X | X | X | X | X | X | X | X | X | X | X | X | X | X | X | X | X | X | X | X | X | X | X |
| S1 | C2 | X | X | X | X | X | X | X | X | X | X | X | X | X | X | X | X | X | X | X | X | X | X | X | X |
| S1 | C3 | X | X | X | X | X | X | X | X | X | X | X | X | X | X | X | X | X | X | X | X | X | X | X | X |
| S1 | A1 | X | X | X | X | X | X | X | X | X | X | X | X | X | X | X | X | X | X | X | X | X | X | X | X |
| S1 | A2 | X | X | X | X | X | X | X | X | X | X | X | X | X | X | X | X | X | X | X | X | X | X | X | X |
| S1 | A3 | X | X | X | X | X | X | X | X | X | X | X | X | X | X | X | X | X | X | X | X | X | X | X | X |
| S1 | S2 | X | X | X | X | X | X | X | X | X | X | X | X | X | X | X | X | X | X | X | X | X | X | X | X |
| S1 | S3 | X | X | X | X | X | X | X | X | X | X | X | X | X | X | X | X | X | X | X | X | X | X | X | X |
| S1 | S4 | X | X | X | X | X | X | X | X | X | X | X | X | X | X | X | X | X | X | X | X | X | X | X | X |
| S1 | E1 | X | X | X | X | X | X | X | X | X | X | X | X | X | X | X | X | X | X | X | X | X | X | X | X |
| S1 | G1 | X | X | X | X | X | X | X | X | X | X | X | X | X | X | X | X | X | X | X | X | X | X | X | X |
| S1 | G2 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | | |
|---|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| S1 | G3 | X | X | X | X | X | X | X | X | X | X | X | X | X | X | X | X | X | X | X | X | X | X | X | X |
| S1 | T1 | X | X | X | X | X | X | X | X | X | X | X | X | X | X | X | X | X | X | X | X | X | X | X | X |
| S1 | T2 | X | X | X | X | X | X | X | X | X | X | X | X | X | X | X | X | X | X | X | X | X | X | X | X |
| S1 | T3 | X | X | X | X | X | X | X | X | X | X | X | X | X | X | X | X | X | X | X | X | X | X | X | X |
| S1 | T4 | X | X | X | X | X | X | X | X | X | X | X | X | X | X | X | X | X | X | X | X | X | X | X | X |
| S1 | P1 | X | X | X | X | X | X | X | X | X | X | X | X | X | X | X | X | X | X | X | X | X | X | X | X |
| S1 | P2 | X | X | X | X | X | X | X | X | X | X | X | X | X | X | X | X | X | X | X | X | X | X | X | X |
| S1 | P3 | X | X | X | X | X | X | X | X | X | X | X | X | X | X | X | X | X | X | X | X | X | X | X | X |
| S1 | E1 | X | X | X | X | X | X | X | X | X | X | X | X | X | X | X | X | X | X | X | X | X | X | X | X |
| S1 | E2 | X | X | X | X | X | X | X | X | X | X | X | X | X | X | X | X | X | X | X | X | X | X | X | X |
| S1 | E3 | X | X | X | X | X | X | X | X | X | X | X | X | X | X | X | X | X | X | X | X | X | X | X | X |
| S2 | C1 | X | X | X | X | X | X | X | X | X | X | X | X | X | X | X | X | X | X | X | X | X | X | X | X |
| S2 | C2 | X | X | X | X | X | X | X | X | X | X | X | X | X | X | X | X | X | X | X | X | X | X | X | X |
| S2 | C3 | X | X | X | X | X | X | X | X | X | X | X | X | X | X | X | X | X | X | X | X | X | X | X | X |
| S2 | A1 | X | X | X | X | X | X | X | X | X | X | X | X | X | X | X | X | X | X | X | X | X | X | X | X |
| S2 | A2 | X | X | X | X | X | X | X | X | X | X | X | X | X | X | X | X | X | X | X | X | X | X | X | X |
| S2 | A3 | X | X | X | X | X | X | X | X | X | X | X | X | X | X | X | X | X | X | X | X | X | X | X | X |
| S2 | S1 | X | X | X | X | X | X | X | X | X | X | X | X | X | X | X | X | X | X | X | X | X | X | X | X |
| S2 | S3 | X | X | X | X | X | X | X | X | X | X | X | X | X | X | X | X | X | X | X | X | X | X | X | X |
| S2 | S4 | X | X | X | X | X | X | X | X | X | X | X | X | X | X | X | X | X | X | X | X | X | X | X | X |
| S2 | F1 | X | X | X | X | X | X | X | X | X | X | X | X | X | X | X | X | X | X | X | X | X | X | X | X |
| S2 | G1 | X | X | X | X | X | X | X | X | X | X | X | X | X | X | X | X | X | X | X | X | X | X | X | X |
| S2 | G2 | X | X | X | X | X | X | X | X | X | X | X | X | X | X | X | X | X | X | X | X | X | X | X | X |
| S2 | G3 | X | X | X | X | X | X | X | X | X | X | X | X | X | X | X | X | X | X | X | X | X | X | X | X |
| S2 | T1 | X | X | X | X | X | X | X | X | X | X | X | X | X | X | X | X | X | X | X | X | X | X | X | X |
| S2 | T2 | X | X | X | X | X | X | X | X | X | X | X | X | X | X | X | X | X | X | X | X | X | X | X | X |
| S2 | T3 | X | X | X | X | X | X | X | X | X | X | X | X | X | X | X | X | X | X | X | X | X | X | X | X |
| S2 | T4 | X | X | X | X | X | X | X | X | X | X | X | X | X | X | X | X | X | X | X | X | X | X | X | X |
| S2 | P1 | X | X | X | X | X | X | X | X | X | X | X | X | X | X | X | X | X | X | X | X | X | X | X | X |
| S2 | P2 | X | X | X | X | X | X | X | X | X | X | X | X | X | X | X | X | X | X | X | X | X | X | X | X |
| S2 | P3 | X | X | X | X | X | X | X | X | X | X | X | X | X | X | X | X | X | X | X | X | X | X | X | X |
| S2 | E1 | X | X | X | X | X | X | X | X | X | X | X | X | X | X | X | X | X | X | X | X | X | X | X | X |
| S2 | E2 | X | X | X | X | X | X | X | X | X | X | X | X | X | X | X | X | X | X | X | X | X | X | X | X |
| S2 | E3 | X | X | X | X | X | X | X | X | X | X | X | X | X | X | X | X | X | X | X | X | X | X | X | X |
| S3 | C1 | X | X | X | X | X | X | X | X | X | X | X | X | X | X | X | X | X | X | X | X | X | X | X | X |
| S3 | C2 | X | X | X | X | X | X | X | X | X | X | X | X | X | X | X | X | X | X | X | X | X | X | X | X |
| S3 | C3 | X | X | X | X | X | X | X | X | X | X | X | X | X | X | X | X | X | X | X | X | X | X | X | X |
| S3 | A1 | X | X | X | X | X | X | X | X | X | X | X | X | X | X | X | X | X | X | X | X | X | X | X | X |
| S3 | A2 | X | X | X | X | X | X | X | X | X | X | X | X | X | X | X | X | X | X | X | X | X | X | X | X |
| S3 | A3 | X | X | X | X | X | X | X | X | X | X | X | X | X | X | X | X | X | X | X | X | X | X | X | X |
| S3 | S1 | X | X | X | X | X | X | X | X | X | X | X | X | X | X | X | X | X | X | X | X | X | X | X | X |
| S3 | S2 | X | X | X | X | X | X | X | X | X | X | X | X | X | X | X | X | X | X | X | X | X | X | X | X |
| S3 | S4 | X | X | X | X | X | X | X | X | X | X | X | X | X | X | X | X | X | X | X | X | X | X | X | X |
| S3 | F1 | X | X | X | X | X | X | X | X | X | X | X | X | X | X | X | X | X | X | X | X | X | X | X | X |
| S3 | G1 | X | X | X | X | X | X | X | X | X | X | X | X | X | X | X | X | X | X | X | X | X | X | X | X |
| S3 | G2 | X | X | X | X | X | X | X | X | X | X | X | X | X | X | X | X | X | X | X | X | X | X | X | X |
| S3 | G3 | X | X | X | X | X | X | X | X | X | X | X | X | X | X | X | X | X | X | X | X | X | X | X | X |
| S3 | T1 | X | X | X | X | X | X | X | X | X | X | X | X | X | X | X | X | X | X | X | X | X | X | X | X |
| S3 | T2 | X | X | X | X | X | X | X | X | X | X | X | X | X | X | X | X | X | X | X | X | X | X | X | X |
| S3 | T3 | X | X | X | X | X | X | X | X | X | X | X | X | X | X | X | X | X | X | X | X | X | X | X | X |
| S3 | T4 | X | X | X | X | X | X | X | X | X | X | X | X | X | X | X | X | X | X | X | X | X | X | X | X |
| S3 | P1 | X | X | X | X | X | X | X | X | X | X | X | X | X | X | X | X | X | X | X | X | X | X | X | X |
| S3 | P2 | X | X | X | X | X | X | X | X | X | X | X | X | X | X | X | X | X | X | X | X | X | X | X | X |
| S3 | P3 | X | X | X | X | X | X | X | X | X | X | X | X | X | X | X | X | X | X | X | X | X | X | X | X |
| S3 | E1 | X | X | X | X | X | X | X | X | X | X | X | X | X | X | X | X | X | X | X | X | X | X | X | X |
| S3 | E2 | X | X | X | X | X | X | X | X | X | X | X | X | X | X | X | X | X | X | X | X | X | X | X | X |
| S3 | E3 | X | X | X | X | X | X | X | X | X | X | X | X | X | X | X | X | X | X | X | X | X | X | X | X |
| S4 | C1 | X | X | X | X | X | X | X | X | X | X | X | X | X | X | X | X | X | X | X | X | X | X | X | X |
| S4 | C2 | X | X | X | X | X | X | X | X | X | X | X | X | X | X | X | X | X | X | X | X | X | X | X | X |
| S4 | C3 | X | X | X | X | X | X | X | X | X | X | X | X | X | X | X | X | X | X | X | X | X | X | X | X |
| S4 | A1 | X | X | X | X | X | X | X | X | X | X | X | X | X | X | X | X | X | X | X | X | X | X | X | X |
| S4 | A2 | X | X | X | X | X | X | X | X | X | X | X | X | X | X | X | X | X | X | X | X | X | X | X | X |
| S4 | A3 | X | X | X | X | X | X | X | X | X | X | X | X | X | X | X | X | X | X | X | X | X | X | X | X |
| S4 | S1 | X | X | X | X | X | X | X | X | X | X | X | X | X | X | X | X | X | X | X | X | X | X | X | X |
| S4 | S2 | X | X | X | X | X | X | X | X | X | X | X | X | X | X | X | X | X | X | X | X | X | X | X | X |
| S4 | S3 | X | X | X | X | X | X | X | X | X | X | X | X | X | X | X | X | X | X | X | X | X | X | X | X |
| S4 | F1 | X | X | X | X | X | X | X | X | X | X | X | X | X | X | X | X | X | X | X | X | X | X | X | X |
| S4 | G1 | X | X | X | X | X | X | X | X | X | X | X | X | X | X | X | X | X | X | X | X | X | X | X | X |
| S4 | G2 | X | X | X | X | X | X | X | X | X | X | X | X | X | X | X | X | X | X | X | X | X | X | X | X |
| S4 | G3 | X | X | X | X | X | X | X | X | X | X | X | X | X | X | X | X | X | X | X | X | X | X | X | X |
| S4 | T1 | X | X | X | X | X | X | X | X | X | X | X | X | X | X | X | X | X | X | X | X | X | X | X | X |
| S4 | T2 | X | X | X | X | X | X | X | X | X | X | X | X | X | X | X | X | X | X | X | X | X | X | X | X |
| S4 | T3 | X | X | X | X | X | X | X | X | X | X | X | X | X | X | X | X | X | X | X | X | X | X | X | X |
| S4 | T4 | X | X | X | X | X | X | X | X | X | X | X | X | X | X | X | X | X | X | X | X | X | X | X | X |
| S4 | P1 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | |
|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| S4 | P2 | X | X | X | X | X | X | X | X | X | X | X | X | X | X | X | X | X | X | X | X | X | X | X | X |
| S4 | P3 | X | X | X | X | X | X | X | X | X | X | X | X | X | X | X | X | X | X | X | X | X | X | X | X |
| S4 | E1 | X | X | X | X | X | X | X | X | X | X | X | X | X | X | X | X | X | X | X | X | X | X | X | X |
| S4 | E2 | X | X | X | X | X | X | X | X | X | X | X | X | X | X | X | X | X | X | X | X | X | X | X | X |
| S4 | E3 | X | X | X | X | X | X | X | X | X | X | X | X | X | X | X | X | X | X | X | X | X | X | X | X |
| F1 | C1 | X | X | X | X | X | X | X | X | X | X | X | X | X | X | X | X | X | X | X | X | X | X | X | X |
| F1 | C2 | X | X | X | X | X | X | X | X | X | X | X | X | X | X | X | X | X | X | X | X | X | X | X | X |
| F1 | C3 | X | X | X | X | X | X | X | X | X | X | X | X | X | X | X | X | X | X | X | X | X | X | X | X |
| F1 | A1 | X | X | X | X | X | X | X | X | X | X | X | X | X | X | X | X | X | X | X | X | X | X | X | X |
| F1 | A2 | X | X | X | X | X | X | X | X | X | X | X | X | X | X | X | X | X | X | X | X | X | X | X | X |
| F1 | A3 | X | X | X | X | X | X | X | X | X | X | X | X | X | X | X | X | X | X | X | X | X | X | X | X |
| F1 | S1 | X | X | X | X | X | X | X | X | X | X | X | X | X | X | X | X | X | X | X | X | X | X | X | X |
| F1 | S2 | X | X | X | X | X | X | X | X | X | X | X | X | X | X | X | X | X | X | X | X | X | X | X | X |
| F1 | S3 | X | X | X | X | X | X | X | X | X | X | X | X | X | X | X | X | X | X | X | X | X | X | X | X |
| F1 | S4 | X | X | X | X | X | X | X | X | X | X | X | X | X | X | X | X | X | X | X | X | X | X | X | X |
| F1 | G1 | X | X | X | X | X | X | X | X | X | X | X | X | X | X | X | X | X | X | X | X | X | X | X | X |
| F1 | G2 | X | X | X | X | X | X | X | X | X | X | X | X | X | X | X | X | X | X | X | X | X | X | X | X |
| F1 | G3 | X | X | X | X | X | X | X | X | X | X | X | X | X | X | X | X | X | X | X | X | X | X | X | X |
| F1 | T1 | X | X | X | X | X | X | X | X | X | X | X | X | X | X | X | X | X | X | X | X | X | X | X | X |
| F1 | T2 | X | X | X | X | X | X | X | X | X | X | X | X | X | X | X | X | X | X | X | X | X | X | X | X |
| F1 | T3 | X | X | X | X | X | X | X | X | X | X | X | X | X | X | X | X | X | X | X | X | X | X | X | X |
| F1 | T4 | X | X | X | X | X | X | X | X | X | X | X | X | X | X | X | X | X | X | X | X | X | X | X | X |
| F1 | P1 | X | X | X | X | X | X | X | X | X | X | X | X | X | X | X | X | X | X | X | X | X | X | X | X |
| F1 | P2 | X | X | X | X | X | X | X | X | X | X | X | X | X | X | X | X | X | X | X | X | X | X | X | X |
| F1 | P3 | X | X | X | X | X | X | X | X | X | X | X | X | X | X | X | X | X | X | X | X | X | X | X | X |
| F1 | E1 | X | X | X | X | X | X | X | X | X | X | X | X | X | X | X | X | X | X | X | X | X | X | X | X |
| F1 | E2 | X | X | X | X | X | X | X | X | X | X | X | X | X | X | X | X | X | X | X | X | X | X | X | X |
| F1 | E3 | X | X | X | X | X | X | X | X | X | X | X | X | X | X | X | X | X | X | X | X | X | X | X | X |
| G1 | C1 | X | X | X | X | X | X | X | X | X | X | X | X | X | X | X | X | X | X | X | X | X | X | X | X |
| G1 | C2 | X | X | X | X | X | X | X | X | X | X | X | X | X | X | X | X | X | X | X | X | X | X | X | X |
| G1 | C3 | X | X | X | X | X | X | X | X | X | X | X | X | X | X | X | X | X | X | X | X | X | X | X | X |
| G1 | A1 | X | X | X | X | X | X | X | X | X | X | X | X | X | X | X | X | X | X | X | X | X | X | X | X |
| G1 | A2 | X | X | X | X | X | X | X | X | X | X | X | X | X | X | X | X | X | X | X | X | X | X | X | X |
| G1 | A3 | X | X | X | X | X | X | X | X | X | X | X | X | X | X | X | X | X | X | X | X | X | X | X | X |
| G1 | S1 | X | X | X | X | X | X | X | X | X | X | X | X | X | X | X | X | X | X | X | X | X | X | X | X |
| G1 | S2 | X | X | X | X | X | X | X | X | X | X | X | X | X | X | X | X | X | X | X | X | X | X | X | X |
| G1 | S3 | X | X | X | X | X | X | X | X | X | X | X | X | X | X | X | X | X | X | X | X | X | X | X | X |
| G1 | S4 | X | X | X | X | X | X | X | X | X | X | X | X | X | X | X | X | X | X | X | X | X | X | X | X |
| G1 | F1 | X | X | X | X | X | X | X | X | X | X | X | X | X | X | X | X | X | X | X | X | X | X | X | X |
| G1 | G2 | X | X | X | X | X | X | X | X | X | X | X | X | X | X | X | X | X | X | X | X | X | X | X | X |
| G1 | G3 | X | X | X | X | X | X | X | X | X | X | X | X | X | X | X | X | X | X | X | X | X | X | X | X |
| G1 | T1 | X | X | X | X | X | X | X | X | X | X | X | X | X | X | X | X | X | X | X | X | X | X | X | X |
| G1 | T2 | X | X | X | X | X | X | X | X | X | X | X | X | X | X | X | X | X | X | X | X | X | X | X | X |
| G1 | T3 | X | X | X | X | X | X | X | X | X | X | X | X | X | X | X | X | X | X | X | X | X | X | X | X |
| G1 | T4 | X | X | X | X | X | X | X | X | X | X | X | X | X | X | X | X | X | X | X | X | X | X | X | X |
| G1 | P1 | X | X | X | X | X | X | X | X | X | X | X | X | X | X | X | X | X | X | X | X | X | X | X | X |
| G1 | P2 | X | X | X | X | X | X | X | X | X | X | X | X | X | X | X | X | X | X | X | X | X | X | X | X |
| G1 | P3 | X | X | X | X | X | X | X | X | X | X | X | X | X | X | X | X | X | X | X | X | X | X | X | X |
| G1 | E1 | X | X | X | X | X | X | X | X | X | X | X | X | X | X | X | X | X | X | X | X | X | X | X | X |
| G1 | E2 | X | X | X | X | X | X | X | X | X | X | X | X | X | X | X | X | X | X | X | X | X | X | X | X |
| G1 | E3 | X | X | X | X | X | X | X | X | X | X | X | X | X | X | X | X | X | X | X | X | X | X | X | X |
| G2 | C1 | X | X | X | X | X | X | X | X | X | X | X | X | X | X | X | X | X | X | X | X | X | X | X | X |
| G2 | C2 | X | X | X | X | X | X | X | X | X | X | X | X | X | X | X | X | X | X | X | X | X | X | X | X |
| G2 | C3 | X | X | X | X | X | X | X | X | X | X | X | X | X | X | X | X | X | X | X | X | X | X | X | X |
| G2 | A1 | X | X | X | X | X | X | X | X | X | X | X | X | X | X | X | X | X | X | X | X | X | X | X | X |
| G2 | A2 | X | X | X | X | X | X | X | X | X | X | X | X | X | X | X | X | X | X | X | X | X | X | X | X |
| G2 | A3 | X | X | X | X | X | X | X | X | X | X | X | X | X | X | X | X | X | X | X | X | X | X | X | X |
| G2 | S1 | X | X | X | X | X | X | X | X | X | X | X | X | X | X | X | X | X | X | X | X | X | X | X | X |
| G2 | S2 | X | X | X | X | X | X | X | X | X | X | X | X | X | X | X | X | X | X | X | X | X | X | X | X |
| G2 | S3 | X | X | X | X | X | X | X | X | X | X | X | X | X | X | X | X | X | X | X | X | X | X | X | X |
| G2 | S4 | X | X | X | X | X | X | X | X | X | X | X | X | X | X | X | X | X | X | X | X | X | X | X | X |
| G2 | F1 | X | X | X | X | X | X | X | X | X | X | X | X | X | X | X | X | X | X | X | X | X | X | X | X |
| G2 | G1 | X | X | X | X | X | X | X | X | X | X | X | X | X | X | X | X | X | X | X | X | X | X | X | X |
| G2 | G3 | X | X | X | X | X | X | X | X | X | X | X | X | X | X | X | X | X | X | X | X | X | X | X | X |
| G2 | T1 | X | X | X | X | X | X | X | X | X | X | X | X | X | X | X | X | X | X | X | X | X | X | X | X |
| G2 | T2 | X | X | X | X | X | X | X | X | X | X | X | X | X | X | X | X | X | X | X | X | X | X | X | X |
| G2 | T3 | X | X | X | X | X | X | X | X | X | X | X | X | X | X | X | X | X | X | X | X | X | X | X | X |
| G2 | T4 | X | X | X | X | X | X | X | X | X | X | X | X | X | X | X | X | X | X | X | X | X | X | X | X |
| G2 | P1 | X | X | X | X | X | X | X | X | X | X | X | X | X | X | X | X | X | X | X | X | X | X | X | X |
| G2 | P2 | X | X | X | X | X | X | X | X | X | X | X | X | X | X | X | X | X | X | X | X | X | X | X | X |
| G2 | P3 | X | X | X | X | X | X | X | X | X | X | X | X | X | X | X | X | X | X | X | X | X | X | X | X |
| G2 | E1 | X | X | X | X | X | X | X | X | X | X | X | X | X | X | X | X | X | X | X | X | X | X | X | X |
| G2 | E2 | X | X | X | X | X | X | X | X | X | X | X | X | X | X | X | X | X | X | X | X | X | X | X | X |
| G2 | E3 | X | X | X | X | X | X | X | X | X | X | X | X | X | X | X | X | X | X | X | X | X | X | X | X |
| G3 | C1 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- |
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| G3 | C2 | X | X | X | X | X | X | X | X | X | X | X | X | X | X | X | X | X | X | X | X | X | X | X | X |
| G3 | C3 | X | X | X | X | X | X | X | X | X | X | X | X | X | X | X | X | X | X | X | X | X | X | X | X |
| G3 | A1 | X | X | X | X | X | X | X | X | X | X | X | X | X | X | X | X | X | X | X | X | X | X | X | X |
| G3 | A2 | X | X | X | X | X | X | X | X | X | X | X | X | X | X | X | X | X | X | X | X | X | X | X | X |
| G3 | A3 | X | X | X | X | X | X | X | X | X | X | X | X | X | X | X | X | X | X | X | X | X | X | X | X |
| G3 | S1 | X | X | X | X | X | X | X | X | X | X | X | X | X | X | X | X | X | X | X | X | X | X | X | X |
| G3 | S2 | X | X | X | X | X | X | X | X | X | X | X | X | X | X | X | X | X | X | X | X | X | X | X | X |
| G3 | S3 | X | X | X | X | X | X | X | X | X | X | X | X | X | X | X | X | X | X | X | X | X | X | X | X |
| G3 | S4 | X | X | X | X | X | X | X | X | X | X | X | X | X | X | X | X | X | X | X | X | X | X | X | X |
| G3 | F1 | X | X | X | X | X | X | X | X | X | X | X | X | X | X | X | X | X | X | X | X | X | X | X | X |
| G3 | G1 | X | X | X | X | X | X | X | X | X | X | X | X | X | X | X | X | X | X | X | X | X | X | X | X |
| G3 | G2 | X | X | X | X | X | X | X | X | X | X | X | X | X | X | X | X | X | X | X | X | X | X | X | X |
| G3 | T1 | X | X | X | X | X | X | X | X | X | X | X | X | X | X | X | X | X | X | X | X | X | X | X | X |
| G3 | T2 | X | X | X | X | X | X | X | X | X | X | X | X | X | X | X | X | X | X | X | X | X | X | X | X |
| G3 | T3 | X | X | X | X | X | X | X | X | X | X | X | X | X | X | X | X | X | X | X | X | X | X | X | X |
| G3 | T4 | X | X | X | X | X | X | X | X | X | X | X | X | X | X | X | X | X | X | X | X | X | X | X | X |
| G3 | P1 | X | X | X | X | X | X | X | X | X | X | X | X | X | X | X | X | X | X | X | X | X | X | X | X |
| G3 | P1 | X | X | X | X | X | X | X | X | X | X | X | X | X | X | X | X | X | X | X | X | X | X | X | X |
| G3 | P2 | X | X | X | X | X | X | X | X | X | X | X | X | X | X | X | X | X | X | X | X | X | X | X | X |
| G3 | P3 | X | X | X | X | X | X | X | X | X | X | X | X | X | X | X | X | X | X | X | X | X | X | X | X |
| G3 | E1 | X | X | X | X | X | X | X | X | X | X | X | X | X | X | X | X | X | X | X | X | X | X | X | X |
| G3 | E2 | X | X | X | X | X | X | X | X | X | X | X | X | X | X | X | X | X | X | X | X | X | X | X | X |
| G3 | E3 | X | X | X | X | X | X | X | X | X | X | X | X | X | X | X | X | X | X | X | X | X | X | X | X |
| T1 | C1 | X | X | X | X | X | X | X | X | X | X | X | X | X | X | X | X | X | X | X | X | X | X | X | X |
| T1 | C2 | X | X | X | X | X | X | X | X | X | X | X | X | X | X | X | X | X | X | X | X | X | X | X | X |
| T1 | C3 | X | X | X | X | X | X | X | X | X | X | X | X | X | X | X | X | X | X | X | X | X | X | X | X |
| T1 | A1 | X | X | X | X | X | X | X | X | X | X | X | X | X | X | X | X | X | X | X | X | X | X | X | X |
| T1 | A2 | X | X | X | X | X | X | X | X | X | X | X | X | X | X | X | X | X | X | X | X | X | X | X | X |
| T1 | A3 | X | X | X | X | X | X | X | X | X | X | X | X | X | X | X | X | X | X | X | X | X | X | X | X |
| T1 | S1 | X | X | X | X | X | X | X | X | X | X | X | X | X | X | X | X | X | X | X | X | X | X | X | X |
| T1 | S2 | X | X | X | X | X | X | X | X | X | X | X | X | X | X | X | X | X | X | X | X | X | X | X | X |
| T1 | S3 | X | X | X | X | X | X | X | X | X | X | X | X | X | X | X | X | X | X | X | X | X | X | X | X |
| T1 | S4 | X | X | X | X | X | X | X | X | X | X | X | X | X | X | X | X | X | X | X | X | X | X | X | X |
| T1 | F1 | X | X | X | X | X | X | X | X | X | X | X | X | X | X | X | X | X | X | X | X | X | X | X | X |
| T1 | G1 | X | X | X | X | X | X | X | X | X | X | X | X | X | X | X | X | X | X | X | X | X | X | X | X |
| T1 | G2 | X | X | X | X | X | X | X | X | X | X | X | X | X | X | X | X | X | X | X | X | X | X | X | X |
| T1 | G3 | X | X | X | X | X | X | X | X | X | X | X | X | X | X | X | X | X | X | X | X | X | X | X | X |
| T1 | T2 | X | X | X | X | X | X | X | X | X | X | X | X | X | X | X | X | X | X | X | X | X | X | X | X |
| T1 | T3 | X | X | X | X | X | X | X | X | X | X | X | X | X | X | X | X | X | X | X | X | X | X | X | X |
| T1 | T4 | X | X | X | X | X | X | X | X | X | X | X | X | X | X | X | X | X | X | X | X | X | X | X | X |
| T1 | P1 | X | X | X | X | X | X | X | X | X | X | X | X | X | X | X | X | X | X | X | X | X | X | X | X |
| T1 | P2 | X | X | X | X | X | X | X | X | X | X | X | X | X | X | X | X | X | X | X | X | X | X | X | X |
| T1 | P3 | X | X | X | X | X | X | X | X | X | X | X | X | X | X | X | X | X | X | X | X | X | X | X | X |
| T1 | E1 | X | X | X | X | X | X | X | X | X | X | X | X | X | X | X | X | X | X | X | X | X | X | X | X |
| T1 | E2 | X | X | X | X | X | X | X | X | X | X | X | X | X | X | X | X | X | X | X | X | X | X | X | X |
| T1 | E3 | X | X | X | X | X | X | X | X | X | X | X | X | X | X | X | X | X | X | X | X | X | X | X | X |
| T2 | C1 | X | X | X | X | X | X | X | X | X | X | X | X | X | X | X | X | X | X | X | X | X | X | X | X |
| T2 | C2 | X | X | X | X | X | X | X | X | X | X | X | X | X | X | X | X | X | X | X | X | X | X | X | X |
| T2 | C3 | X | X | X | X | X | X | X | X | X | X | X | X | X | X | X | X | X | X | X | X | X | X | X | X |
| T2 | A1 | X | X | X | X | X | X | X | X | X | X | X | X | X | X | X | X | X | X | X | X | X | X | X | X |
| T2 | A2 | X | X | X | X | X | X | X | X | X | X | X | X | X | X | X | X | X | X | X | X | X | X | X | X |
| T2 | A3 | X | X | X | X | X | X | X | X | X | X | X | X | X | X | X | X | X | X | X | X | X | X | X | X |
| T2 | S1 | X | X | X | X | X | X | X | X | X | X | X | X | X | X | X | X | X | X | X | X | X | X | X | X |
| T2 | S2 | X | X | X | X | X | X | X | X | X | X | X | X | X | X | X | X | X | X | X | X | X | X | X | X |
| T2 | S3 | X | X | X | X | X | X | X | X | X | X | X | X | X | X | X | X | X | X | X | X | X | X | X | X |
| T2 | S4 | X | X | X | X | X | X | X | X | X | X | X | X | X | X | X | X | X | X | X | X | X | X | X | X |
| T2 | F1 | X | X | X | X | X | X | X | X | X | X | X | X | X | X | X | X | X | X | X | X | X | X | X | X |
| T2 | G1 | X | X | X | X | X | X | X | X | X | X | X | X | X | X | X | X | X | X | X | X | X | X | X | X |
| T2 | G2 | X | X | X | X | X | X | X | X | X | X | X | X | X | X | X | X | X | X | X | X | X | X | X | X |
| T2 | G3 | X | X | X | X | X | X | X | X | X | X | X | X | X | X | X | X | X | X | X | X | X | X | X | X |
| T2 | T1 | X | X | X | X | X | X | X | X | X | X | X | X | X | X | X | X | X | X | X | X | X | X | X | X |
| T2 | T3 | X | X | X | X | X | X | X | X | X | X | X | X | X | X | X | X | X | X | X | X | X | X | X | X |
| T2 | T4 | X | X | X | X | X | X | X | X | X | X | X | X | X | X | X | X | X | X | X | X | X | X | X | X |
| T2 | P1 | X | X | X | X | X | X | X | X | X | X | X | X | X | X | X | X | X | X | X | X | X | X | X | X |
| T2 | P2 | X | X | X | X | X | X | X | X | X | X | X | X | X | X | X | X | X | X | X | X | X | X | X | X |
| T2 | P3 | X | X | X | X | X | X | X | X | X | X | X | X | X | X | X | X | X | X | X | X | X | X | X | X |
| T2 | E1 | X | X | X | X | X | X | X | X | X | X | X | X | X | X | X | X | X | X | X | X | X | X | X | X |
| T2 | E2 | X | X | X | X | X | X | X | X | X | X | X | X | X | X | X | X | X | X | X | X | X | X | X | X |
| T2 | E3 | X | X | X | X | X | X | X | X | X | X | X | X | X | X | X | X | X | X | X | X | X | X | X | X |
| T3 | C1 | X | X | X | X | X | X | X | X | X | X | X | X | X | X | X | X | X | X | X | X | X | X | X | X |
| T3 | C2 | X | X | X | X | X | X | X | X | X | X | X | X | X | X | X | X | X | X | X | X | X | X | X | X |
| T3 | C3 | X | X | X | X | X | X | X | X | X | X | X | X | X | X | X | X | X | X | X | X | X | X | X | X |
| T3 | A1 | X | X | X | X | X | X | X | X | X | X | X | X | X | X | X | X | X | X | X | X | X | X | X | X |
| T3 | A2 | X | X | X | X | X | X | X | X | X | X | X | X | X | X | X | X | X | X | X | X | X | X | X | X |
| T3 | A3 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | | |
|---|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| T3 | S1 | X | X | X | X | X | X | X | X | X | X | X | X | X | X | X | X | X | X | X | X | X | X | X | X |
| T3 | S2 | X | X | X | X | X | X | X | X | X | X | X | X | X | X | X | X | X | X | X | X | X | X | X | X |
| T3 | S3 | X | X | X | X | X | X | X | X | X | X | X | X | X | X | X | X | X | X | X | X | X | X | X | X |
| T3 | S4 | X | X | X | X | X | X | X | X | X | X | X | X | X | X | X | X | X | X | X | X | X | X | X | X |
| T3 | F1 | X | X | X | X | X | X | X | X | X | X | X | X | X | X | X | X | X | X | X | X | X | X | X | X |
| T3 | G1 | X | X | X | X | X | X | X | X | X | X | X | X | X | X | X | X | X | X | X | X | X | X | X | X |
| T3 | G2 | X | X | X | X | X | X | X | X | X | X | X | X | X | X | X | X | X | X | X | X | X | X | X | X |
| T3 | G3 | X | X | X | X | X | X | X | X | X | X | X | X | X | X | X | X | X | X | X | X | X | X | X | X |
| T3 | T1 | X | X | X | X | X | X | X | X | X | X | X | X | X | X | X | X | X | X | X | X | X | X | X | X |
| T3 | T2 | X | X | X | X | X | X | X | X | X | X | X | X | X | X | X | X | X | X | X | X | X | X | X | X |
| T3 | T4 | X | X | X | X | X | X | X | X | X | X | X | X | X | X | X | X | X | X | X | X | X | X | X | X |
| T3 | P1 | X | X | X | X | X | X | X | X | X | X | X | X | X | X | X | X | X | X | X | X | X | X | X | X |
| T3 | P2 | X | X | X | X | X | X | X | X | X | X | X | X | X | X | X | X | X | X | X | X | X | X | X | X |
| T3 | P3 | X | X | X | X | X | X | X | X | X | X | X | X | X | X | X | X | X | X | X | X | X | X | X | X |
| T3 | E1 | X | X | X | X | X | X | X | X | X | X | X | X | X | X | X | X | X | X | X | X | X | X | X | X |
| T3 | E2 | X | X | X | X | X | X | X | X | X | X | X | X | X | X | X | X | X | X | X | X | X | X | X | X |
| T3 | E3 | X | X | X | X | X | X | X | X | X | X | X | X | X | X | X | X | X | X | X | X | X | X | X | X |
| T4 | C1 | X | X | X | X | X | X | X | X | X | X | X | X | X | X | X | X | X | X | X | X | X | X | X | X |
| T4 | C2 | X | X | X | X | X | X | X | X | X | X | X | X | X | X | X | X | X | X | X | X | X | X | X | X |
| T4 | C3 | X | X | X | X | X | X | X | X | X | X | X | X | X | X | X | X | X | X | X | X | X | X | X | X |
| T4 | A1 | X | X | X | X | X | X | X | X | X | X | X | X | X | X | X | X | X | X | X | X | X | X | X | X |
| T4 | A2 | X | X | X | X | X | X | X | X | X | X | X | X | X | X | X | X | X | X | X | X | X | X | X | X |
| T4 | A3 | X | X | X | X | X | X | X | X | X | X | X | X | X | X | X | X | X | X | X | X | X | X | X | X |
| T4 | S1 | X | X | X | X | X | X | X | X | X | X | X | X | X | X | X | X | X | X | X | X | X | X | X | X |
| T4 | S2 | X | X | X | X | X | X | X | X | X | X | X | X | X | X | X | X | X | X | X | X | X | X | X | X |
| T4 | S3 | X | X | X | X | X | X | X | X | X | X | X | X | X | X | X | X | X | X | X | X | X | X | X | X |
| T4 | S4 | X | X | X | X | X | X | X | X | X | X | X | X | X | X | X | X | X | X | X | X | X | X | X | X |
| T4 | F1 | X | X | X | X | X | X | X | X | X | X | X | X | X | X | X | X | X | X | X | X | X | X | X | X |
| T4 | G1 | X | X | X | X | X | X | X | X | X | X | X | X | X | X | X | X | X | X | X | X | X | X | X | X |
| T4 | G2 | X | X | X | X | X | X | X | X | X | X | X | X | X | X | X | X | X | X | X | X | X | X | X | X |
| T4 | G3 | X | X | X | X | X | X | X | X | X | X | X | X | X | X | X | X | X | X | X | X | X | X | X | X |
| T4 | T1 | X | X | X | X | X | X | X | X | X | X | X | X | X | X | X | X | X | X | X | X | X | X | X | X |
| T4 | T2 | X | X | X | X | X | X | X | X | X | X | X | X | X | X | X | X | X | X | X | X | X | X | X | X |
| T4 | T3 | X | X | X | X | X | X | X | X | X | X | X | X | X | X | X | X | X | X | X | X | X | X | X | X |
| T4 | P1 | X | X | X | X | X | X | X | X | X | X | X | X | X | X | X | X | X | X | X | X | X | X | X | X |
| T4 | P2 | X | X | X | X | X | X | X | X | X | X | X | X | X | X | X | X | X | X | X | X | X | X | X | X |
| T4 | P3 | X | X | X | X | X | X | X | X | X | X | X | X | X | X | X | X | X | X | X | X | X | X | X | X |
| T4 | E1 | X | X | X | X | X | X | X | X | X | X | X | X | X | X | X | X | X | X | X | X | X | X | X | X |
| T4 | E2 | X | X | X | X | X | X | X | X | X | X | X | X | X | X | X | X | X | X | X | X | X | X | X | X |
| T4 | E3 | X | X | X | X | X | X | X | X | X | X | X | X | X | X | X | X | X | X | X | X | X | X | X | X |
| P1 | C1 | X | X | X | X | X | X | X | X | X | X | X | X | X | X | X | X | X | X | X | X | X | X | X | X |
| P1 | C2 | X | X | X | X | X | X | X | X | X | X | X | X | X | X | X | X | X | X | X | X | X | X | X | X |
| P1 | C3 | X | X | X | X | X | X | X | X | X | X | X | X | X | X | X | X | X | X | X | X | X | X | X | X |
| P1 | A1 | X | X | X | X | X | X | X | X | X | X | X | X | X | X | X | X | X | X | X | X | X | X | X | X |
| P1 | A2 | X | X | X | X | X | X | X | X | X | X | X | X | X | X | X | X | X | X | X | X | X | X | X | X |
| P1 | A3 | X | X | X | X | X | X | X | X | X | X | X | X | X | X | X | X | X | X | X | X | X | X | X | X |
| P1 | S1 | X | X | X | X | X | X | X | X | X | X | X | X | X | X | X | X | X | X | X | X | X | X | X | X |
| P1 | S2 | X | X | X | X | X | X | X | X | X | X | X | X | X | X | X | X | X | X | X | X | X | X | X | X |
| P1 | S3 | X | X | X | X | X | X | X | X | X | X | X | X | X | X | X | X | X | X | X | X | X | X | X | X |
| P1 | S4 | X | X | X | X | X | X | X | X | X | X | X | X | X | X | X | X | X | X | X | X | X | X | X | X |
| P1 | F1 | X | X | X | X | X | X | X | X | X | X | X | X | X | X | X | X | X | X | X | X | X | X | X | X |
| P1 | G1 | X | X | X | X | X | X | X | X | X | X | X | X | X | X | X | X | X | X | X | X | X | X | X | X |
| P1 | G2 | X | X | X | X | X | X | X | X | X | X | X | X | X | X | X | X | X | X | X | X | X | X | X | X |
| P1 | G3 | X | X | X | X | X | X | X | X | X | X | X | X | X | X | X | X | X | X | X | X | X | X | X | X |
| P1 | T1 | X | X | X | X | X | X | X | X | X | X | X | X | X | X | X | X | X | X | X | X | X | X | X | X |
| P1 | T2 | X | X | X | X | X | X | X | X | X | X | X | X | X | X | X | X | X | X | X | X | X | X | X | X |
| P1 | T3 | X | X | X | X | X | X | X | X | X | X | X | X | X | X | X | X | X | X | X | X | X | X | X | X |
| P1 | T4 | X | X | X | X | X | X | X | X | X | X | X | X | X | X | X | X | X | X | X | X | X | X | X | X |
| P1 | P2 | X | X | X | X | X | X | X | X | X | X | X | X | X | X | X | X | X | X | X | X | X | X | X | X |
| P1 | P3 | X | X | X | X | X | X | X | X | X | X | X | X | X | X | X | X | X | X | X | X | X | X | X | X |
| P1 | E1 | X | X | X | X | X | X | X | X | X | X | X | X | X | X | X | X | X | X | X | X | X | X | X | X |
| P1 | E2 | X | X | X | X | X | X | X | X | X | X | X | X | X | X | X | X | X | X | X | X | X | X | X | X |
| P1 | E3 | X | X | X | X | X | X | X | X | X | X | X | X | X | X | X | X | X | X | X | X | X | X | X | X |
| P2 | C1 | X | X | X | X | X | X | X | X | X | X | X | X | X | X | X | X | X | X | X | X | X | X | X | X |
| P2 | C2 | X | X | X | X | X | X | X | X | X | X | X | X | X | X | X | X | X | X | X | X | X | X | X | X |
| P2 | C3 | X | X | X | X | X | X | X | X | X | X | X | X | X | X | X | X | X | X | X | X | X | X | X | X |
| P2 | A1 | X | X | X | X | X | X | X | X | X | X | X | X | X | X | X | X | X | X | X | X | X | X | X | X |
| P2 | A2 | X | X | X | X | X | X | X | X | X | X | X | X | X | X | X | X | X | X | X | X | X | X | X | X |
| P2 | A3 | X | X | X | X | X | X | X | X | X | X | X | X | X | X | X | X | X | X | X | X | X | X | X | X |
| P2 | S1 | X | X | X | X | X | X | X | X | X | X | X | X | X | X | X | X | X | X | X | X | X | X | X | X |
| P2 | S2 | X | X | X | X | X | X | X | X | X | X | X | X | X | X | X | X | X | X | X | X | X | X | X | X |
| P2 | S3 | X | X | X | X | X | X | X | X | X | X | X | X | X | X | X | X | X | X | X | X | X | X | X | X |
| P2 | S4 | X | X | X | X | X | X | X | X | X | X | X | X | X | X | X | X | X | X | X | X | X | X | X | X |
| P2 | F1 | X | X | X | X | X | X | X | X | X | X | X | X | X | X | X | X | X | X | X | X | X | X | X | X |
| P2 | G1 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | | |
|---|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| P2 | G2 | X | X | X | X | X | X | X | X | X | X | X | X | X | X | X | X | X | X | X | X | X | X | X | X |
| P2 | G3 | X | X | X | X | X | X | X | X | X | X | X | X | X | X | X | X | X | X | X | X | X | X | X | X |
| P2 | T1 | X | X | X | X | X | X | X | X | X | X | X | X | X | X | X | X | X | X | X | X | X | X | X | X |
| P2 | T2 | X | X | X | X | X | X | X | X | X | X | X | X | X | X | X | X | X | X | X | X | X | X | X | X |
| P2 | T3 | X | X | X | X | X | X | X | X | X | X | X | X | X | X | X | X | X | X | X | X | X | X | X | X |
| P2 | T4 | X | X | X | X | X | X | X | X | X | X | X | X | X | X | X | X | X | X | X | X | X | X | X | X |
| P2 | P1 | X | X | X | X | X | X | X | X | X | X | X | X | X | X | X | X | X | X | X | X | X | X | X | X |
| P2 | P3 | X | X | X | X | X | X | X | X | X | X | X | X | X | X | X | X | X | X | X | X | X | X | X | X |
| P2 | E1 | X | X | X | X | X | X | X | X | X | X | X | X | X | X | X | X | X | X | X | X | X | X | X | X |
| P2 | E2 | X | X | X | X | X | X | X | X | X | X | X | X | X | X | X | X | X | X | X | X | X | X | X | X |
| P2 | E3 | X | X | X | X | X | X | X | X | X | X | X | X | X | X | X | X | X | X | X | X | X | X | X | X |
| P3 | C1 | X | X | X | X | X | X | X | X | X | X | X | X | X | X | X | X | X | X | X | X | X | X | X | X |
| P3 | C2 | X | X | X | X | X | X | X | X | X | X | X | X | X | X | X | X | X | X | X | X | X | X | X | X |
| P3 | C3 | X | X | X | X | X | X | X | X | X | X | X | X | X | X | X | X | X | X | X | X | X | X | X | X |
| P3 | A1 | X | X | X | X | X | X | X | X | X | X | X | X | X | X | X | X | X | X | X | X | X | X | X | X |
| P3 | A2 | X | X | X | X | X | X | X | X | X | X | X | X | X | X | X | X | X | X | X | X | X | X | X | X |
| P3 | A3 | X | X | X | X | X | X | X | X | X | X | X | X | X | X | X | X | X | X | X | X | X | X | X | X |
| P3 | S1 | X | X | X | X | X | X | X | X | X | X | X | X | X | X | X | X | X | X | X | X | X | X | X | X |
| P3 | S2 | X | X | X | X | X | X | X | X | X | X | X | X | X | X | X | X | X | X | X | X | X | X | X | X |
| P3 | S3 | X | X | X | X | X | X | X | X | X | X | X | X | X | X | X | X | X | X | X | X | X | X | X | X |
| P3 | S4 | X | X | X | X | X | X | X | X | X | X | X | X | X | X | X | X | X | X | X | X | X | X | X | X |
| P3 | F1 | X | X | X | X | X | X | X | X | X | X | X | X | X | X | X | X | X | X | X | X | X | X | X | X |
| P3 | G1 | X | X | X | X | X | X | X | X | X | X | X | X | X | X | X | X | X | X | X | X | X | X | X | X |
| P3 | G2 | X | X | X | X | X | X | X | X | X | X | X | X | X | X | X | X | X | X | X | X | X | X | X | X |
| P3 | G3 | X | X | X | X | X | X | X | X | X | X | X | X | X | X | X | X | X | X | X | X | X | X | X | X |
| P3 | T1 | X | X | X | X | X | X | X | X | X | X | X | X | X | X | X | X | X | X | X | X | X | X | X | X |
| P3 | T2 | X | X | X | X | X | X | X | X | X | X | X | X | X | X | X | X | X | X | X | X | X | X | X | X |
| P3 | T3 | X | X | X | X | X | X | X | X | X | X | X | X | X | X | X | X | X | X | X | X | X | X | X | X |
| P3 | T4 | X | X | X | X | X | X | X | X | X | X | X | X | X | X | X | X | X | X | X | X | X | X | X | X |
| P3 | P1 | X | X | X | X | X | X | X | X | X | X | X | X | X | X | X | X | X | X | X | X | X | X | X | X |
| P3 | P2 | X | X | X | X | X | X | X | X | X | X | X | X | X | X | X | X | X | X | X | X | X | X | X | X |
| P3 | E1 | X | X | X | X | X | X | X | X | X | X | X | X | X | X | X | X | X | X | X | X | X | X | X | X |
| P3 | E2 | X | X | X | X | X | X | X | X | X | X | X | X | X | X | X | X | X | X | X | X | X | X | X | X |
| P3 | E3 | X | X | X | X | X | X | X | X | X | X | X | X | X | X | X | X | X | X | X | X | X | X | X | X |
| E1 | C1 | X | X | X | X | X | X | X | X | X | X | X | X | X | X | X | X | X | X | X | X | X | X | X | X |
| E1 | C2 | X | X | X | X | X | X | X | X | X | X | X | X | X | X | X | X | X | X | X | X | X | X | X | X |
| E1 | C3 | X | X | X | X | X | X | X | X | X | X | X | X | X | X | X | X | X | X | X | X | X | X | X | X |
| E1 | A1 | X | X | X | X | X | X | X | X | X | X | X | X | X | X | X | X | X | X | X | X | X | X | X | X |
| E1 | A2 | X | X | X | X | X | X | X | X | X | X | X | X | X | X | X | X | X | X | X | X | X | X | X | X |
| E1 | A3 | X | X | X | X | X | X | X | X | X | X | X | X | X | X | X | X | X | X | X | X | X | X | X | X |
| E1 | S1 | X | X | X | X | X | X | X | X | X | X | X | X | X | X | X | X | X | X | X | X | X | X | X | X |
| E1 | S2 | X | X | X | X | X | X | X | X | X | X | X | X | X | X | X | X | X | X | X | X | X | X | X | X |
| E1 | S3 | X | X | X | X | X | X | X | X | X | X | X | X | X | X | X | X | X | X | X | X | X | X | X | X |
| E1 | S4 | X | X | X | X | X | X | X | X | X | X | X | X | X | X | X | X | X | X | X | X | X | X | X | X |
| E1 | F1 | X | X | X | X | X | X | X | X | X | X | X | X | X | X | X | X | X | X | X | X | X | X | X | X |
| E1 | G1 | X | X | X | X | X | X | X | X | X | X | X | X | X | X | X | X | X | X | X | X | X | X | X | X |
| E1 | G2 | X | X | X | X | X | X | X | X | X | X | X | X | X | X | X | X | X | X | X | X | X | X | X | X |
| E1 | G3 | X | X | X | X | X | X | X | X | X | X | X | X | X | X | X | X | X | X | X | X | X | X | X | X |
| E1 | T1 | X | X | X | X | X | X | X | X | X | X | X | X | X | X | X | X | X | X | X | X | X | X | X | X |
| E1 | T2 | X | X | X | X | X | X | X | X | X | X | X | X | X | X | X | X | X | X | X | X | X | X | X | X |
| E1 | T3 | X | X | X | X | X | X | X | X | X | X | X | X | X | X | X | X | X | X | X | X | X | X | X | X |
| E1 | T4 | X | X | X | X | X | X | X | X | X | X | X | X | X | X | X | X | X | X | X | X | X | X | X | X |
| E1 | P1 | X | X | X | X | X | X | X | X | X | X | X | X | X | X | X | X | X | X | X | X | X | X | X | X |
| E1 | P2 | X | X | X | X | X | X | X | X | X | X | X | X | X | X | X | X | X | X | X | X | X | X | X | X |
| E1 | P3 | X | X | X | X | X | X | X | X | X | X | X | X | X | X | X | X | X | X | X | X | X | X | X | X |
| E1 | E2 | X | X | X | X | X | X | X | X | X | X | X | X | X | X | X | X | X | X | X | X | X | X | X | X |
| E1 | E3 | X | X | X | X | X | X | X | X | X | X | X | X | X | X | X | X | X | X | X | X | X | X | X | X |
| E2 | C1 | X | X | X | X | X | X | X | X | X | X | X | X | X | X | X | X | X | X | X | X | X | X | X | X |
| E2 | C2 | X | X | X | X | X | X | X | X | X | X | X | X | X | X | X | X | X | X | X | X | X | X | X | X |
| E2 | C3 | X | X | X | X | X | X | X | X | X | X | X | X | X | X | X | X | X | X | X | X | X | X | X | X |
| E2 | A1 | X | X | X | X | X | X | X | X | X | X | X | X | X | X | X | X | X | X | X | X | X | X | X | X |
| E2 | A2 | X | X | X | X | X | X | X | X | X | X | X | X | X | X | X | X | X | X | X | X | X | X | X | X |
| E2 | A3 | X | X | X | X | X | X | X | X | X | X | X | X | X | X | X | X | X | X | X | X | X | X | X | X |
| E2 | S1 | X | X | X | X | X | X | X | X | X | X | X | X | X | X | X | X | X | X | X | X | X | X | X | X |
| E2 | S2 | X | X | X | X | X | X | X | X | X | X | X | X | X | X | X | X | X | X | X | X | X | X | X | X |
| E2 | S3 | X | X | X | X | X | X | X | X | X | X | X | X | X | X | X | X | X | X | X | X | X | X | X | X |
| E2 | S4 | X | X | X | X | X | X | X | X | X | X | X | X | X | X | X | X | X | X | X | X | X | X | X | X |
| E2 | F1 | X | X | X | X | X | X | X | X | X | X | X | X | X | X | X | X | X | X | X | X | X | X | X | X |
| E2 | G1 | X | X | X | X | X | X | X | X | X | X | X | X | X | X | X | X | X | X | X | X | X | X | X | X |
| E2 | G2 | X | X | X | X | X | X | X | X | X | X | X | X | X | X | X | X | X | X | X | X | X | X | X | X |
| E2 | G3 | X | X | X | X | X | X | X | X | X | X | X | X | X | X | X | X | X | X | X | X | X | X | X | X |
| E2 | T1 | X | X | X | X | X | X | X | X | X | X | X | X | X | X | X | X | X | X | X | X | X | X | X | X |
| E2 | T2 | X | X | X | X | X | X | X | X | X | X | X | X | X | X | X | X | X | X | X | X | X | X | X | X |
| E2 | T3 | X | X | X | X | X | X | X | X | X | X | X | X | X | X | X | X | X | X | X | X | X | X | X | X |
| E2 | T4 | X | X | X | X | X | X | X | X | X | X | X | X | X | X | X | X | X | X | X | X | X | X | X | X |

TABLE 4-continued

| Gene 1 | Gene 2 | Gene 3 | | | | | | | | | | | | | | | | | | | | | | |
|---|---|---|---|---|---|---|---|---|---|---|---|---|---|---|---|---|---|---|---|---|---|---|---|---|
| | | C1 | C2 | C3 | A1 | A2 | A3 | S1 | S2 | S3 | S4 | F1 | G1 | G2 | G3 | T1 | T2 | T3 | T4 | P1 | P2 | P3 | E1 | E2 | E3 |
| E2 | P1 | X | X | X | X | X | X | X | X | X | X | X | X | X | X | X | X | X | X | X | X | X | X | X | X |
| E2 | P2 | X | X | X | X | X | X | X | X | X | X | X | X | X | X | X | X | X | X | X | X | X | X | X | X |
| E2 | P3 | X | X | X | X | X | X | X | X | X | X | X | X | X | X | X | X | X | X | X | X | X | X | X | X |
| E2 | E1 | X | X | X | X | X | X | X | X | X | X | X | X | X | X | X | X | X | X | X | X | X | X | X | X |
| E2 | E3 | X | X | X | X | X | X | X | X | X | X | X | X | X | X | X | X | X | X | X | X | X | X | X | X |
| E3 | C1 | X | X | X | X | X | X | X | X | X | X | X | X | X | X | X | X | X | X | X | X | X | X | X | X |
| E3 | C2 | X | X | X | X | X | X | X | X | X | X | X | X | X | X | X | X | X | X | X | X | X | X | X | X |
| E3 | C3 | X | X | X | X | X | X | X | X | X | X | X | X | X | X | X | X | X | X | X | X | X | X | X | X |
| E3 | A1 | X | X | X | X | X | X | X | X | X | X | X | X | X | X | X | X | X | X | X | X | X | X | X | X |
| E3 | A2 | X | X | X | X | X | X | X | X | X | X | X | X | X | X | X | X | X | X | X | X | X | X | X | X |
| E3 | A3 | X | X | X | X | X | X | X | X | X | X | X | X | X | X | X | X | X | X | X | X | X | X | X | X |
| E3 | S1 | X | X | X | X | X | X | X | X | X | X | X | X | X | X | X | X | X | X | X | X | X | X | X | X |
| E3 | S2 | X | X | X | X | X | X | X | X | X | X | X | X | X | X | X | X | X | X | X | X | X | X | X | X |
| E3 | S3 | X | X | X | X | X | X | X | X | X | X | X | X | X | X | X | X | X | X | X | X | X | X | X | X |
| E3 | S4 | X | X | X | X | X | X | X | X | X | X | X | X | X | X | X | X | X | X | X | X | X | X | X | X |
| E3 | F1 | X | X | X | X | X | X | X | X | X | X | X | X | X | X | X | X | X | X | X | X | X | X | X | X |
| E3 | G1 | X | X | X | X | X | X | X | X | X | X | X | X | X | X | X | X | X | X | X | X | X | X | X | X |
| E3 | G2 | X | X | X | X | X | X | X | X | X | X | X | X | X | X | X | X | X | X | X | X | X | X | X | X |
| E3 | G3 | X | X | X | X | X | X | X | X | X | X | X | X | X | X | X | X | X | X | X | X | X | X | X | X |
| E3 | T1 | X | X | X | X | X | X | X | X | X | X | X | X | X | X | X | X | X | X | X | X | X | X | X | X |
| E3 | T2 | X | X | X | X | X | X | X | X | X | X | X | X | X | X | X | X | X | X | X | X | X | X | X | X |
| E3 | T3 | X | X | X | X | X | X | X | X | X | X | X | X | X | X | X | X | X | X | X | X | X | X | X | X |
| E3 | T4 | X | X | X | X | X | X | X | X | X | X | X | X | X | X | X | X | X | X | X | X | X | X | X | X |
| E3 | P1 | X | X | X | X | X | X | X | X | X | X | X | X | X | X | X | X | X | X | X | X | X | X | X | X |
| E3 | P2 | X | X | X | X | X | X | X | X | X | X | X | X | X | X | X | X | X | X | X | X | X | X | X | X |
| E3 | P3 | X | X | X | X | X | X | X | X | X | X | X | X | X | X | X | X | X | X | X | X | X | X | X | X |
| E3 | E1 | X | X | X | X | X | X | X | X | X | X | X | X | X | X | X | X | X | X | X | X | X | X | X | X |
| E3 | E2 | X | X | X | X | X | X | X | X | X | X | X | X | X | X | X | X | X | X | X | X | X | X | X | X |

In one aspect of the above embodiment, the engineered cell that has targeted modulation of three genes further has targeted modulation of a fourth gene. In one aspect, the fourth gene is selected from the group consisting of C1, C2, C3, A1, A2, A3, S1, S2, S3, S4, F1, G1, G2, G3, T1, T2, T3, T4, P1, P2, P3, E1, E2, and E3.

In one aspect of the above embodiment, the engineered cell that has targeted modulation of four genes further has targeted modulation of a fifth gene. In one aspect, the fifth gene is selected from the group consisting of C1, C2, C3, A1, A2, A3, S1, S2, S3, S4, F1, G1, G2, G3, T1, T2, T3, T4, P1, P2, P3, E1, E2, and E3.

In one aspect of the above embodiment, the engineered cell that has targeted modulation of five genes further has targeted modulation of a sixth gene. In one aspect, the sixth gene is selected from the group consisting of C1, C2, C3, A1, A2, A3, S1, S2, S3, S4, F1, G1, G2, G3, T1, T2, T3, T4, P1, P2, P3, E1, E2, and E3.

In one aspect of the above embodiment, the engineered cell that has targeted modulation of six genes further has targeted modulation of a seventh gene. In one aspect, the seventh gene is selected from the group consisting of C1, C2, C3, A1, A2, A3, S1, S2, S3, S4, F1, G1, G2, G3, T1, T2, T3, T4, P1, P2, P3, E1, E2, and E3.

In any of the above embodiments, the engineered cell can optionally have targeted modulation of one or more genes selected from the group consisting of C4-C8, A4-A6, F2-F9, G4-G6, P4-P9 and E4-E5.

In one embodiment, the engineered cell has targeted modulation of one, two, three, four, five, six, seven or eight genes selected from the group consisting of C1-C8, A1-A6, S1-S4, F1-F9, G1-G6, T1-T4, P1-P9, and E1-E5.

In one embodiment, the engineered cell has targeted modulation of either or both of U1 and U2 (as shown in the table below), U1 and one of U2-U4, or any of U1-U4. In one embodiment, the engineered has modulation of one, two, three, four, five, six, seven or eight genes selected from the group consisting of C1-C8, A1-A6, S1-S4, F1-F9, G1-G6, T1-T4, P1-P9, E1-E5, and U1-U4.

| No. | Gene(s) | Regulation | Function |
|---|---|---|---|
| U1 | GLUT1 | Down | also known as solute carrier family 2, facilitated glucose transporter member 1 (SLC2A1) |
| U2 | GLUT2 | Up | also known as solute carrier family 2 (facilitated glucose transporter), member 2 (SLC2A2) is a transmembrane carrier protein that enables protein facilitated glucose movement across cell membranes |
| U3 | GLUT3 | Up | encoded by the SLC2A3 gene and facilitates the transport of glucose across the plasma membranes of mammalian cells |
| U4 | GLUT4 | Up | Encoded by the GLUT4 gene and is the insulin-regulated glucose transporter found primarily in adipose tissues and striated muscle |

In some embodiments, the engineered cell is cultured in a medium that includes supplements suitable for its growth and protein production. Non-limiting examples of such supplements include:

| No. | Supplement | Description |
|---|---|---|
| M1 | Ubiquinone | increases NADH production |
| M2 | Aspartic acid | Increases cellular ability to manage electrons |
| M3 | Rapamycin | Delays the viability drop and apoptosis induction. In particular, the improved cell viability of an antibody-producing rCHO cell line resulting from the rapamycin treatment leads to increased antibody concentration |

In one embodiment, the engineered cell has targeted modulation of genes of any of the following lists:

| Engineered cell | Modulation of genes | Optional Supplement in Medium |
| --- | --- | --- |
| 1 | C3, C5, U2, C2, E2, G2, A2, A1, S1, S3, U1, P1, and T1 | M1, and M2 |
| 2 | P1, and T1 | M2 |
| 3 | U2, E2, A2, A1, and S1 | |
| 4 | C3, C5, U2, G2, A1, and S3 | M1, and M2 |
| 5 | U2, E2, and S1 | M1 |

In a preferred aspect of any of the above embodiments, the modulation is achieved by mutating or deleting at least part of the gene for down-regulation or introducing one or more copies of the gene or its coding sequence for up-regulation.

In one embodiment, the engineered cell further includes an exogenous coding sequence ("gene of interest" or GOI). The GOI can be included on a separate vector (e.g., plasmid) or integrated to one of the chromosomes of the cell. In one embodiment, the GOI encodes a polypeptide which can be a therapeutic protein. In one embodiment, the GOI encodes an antibody or an antibody fragment.

In one embodiment, the engineered cell is a mammalian cell and preferably a human cell. In one embodiment, the cell is a CHO cell, such as CHO lineage-DG44, DxB11, CHOM (Selexis), CHOs (Life Tech), CHOK1SV (Lonza), or CHOZN (Sigma). In one embodiment, the cell is NSO-mouse, BHK, PerC6, K562, or Cos1&7 cells.

Methods of using any cell of the present disclosure for expressing or producing a product of the GOI are also provided.

III. Methods for Up- or Down-Regulating a Gene in a Cell

Methods for up-regulating a gene (e.g., increasing the biological activity of the gene) in a cell is known in the art. In one aspect, the gene level is increased by increasing the amount of a polynucleotide encoding gene, as provided above, wherein that polynucleotide is expressed such that new gene is produced. In another aspect, increasing the gene level is increased by increasing the transcription of a polynucleotide encoding gene, or alternatively translation of gene, or alternatively post-translational modification, activation or appropriate folding of gene. In yet another aspect, increasing gene level is increased by increasing the binding of the protein to appropriate cofactor, receptor, activator, ligand, or any molecule that is involved in the protein's biological functioning. In some embodiments, increasing the binding of gene to the appropriate molecule is increasing the amount of the molecule. In one aspect of the embodiments, the molecule is the gene protein. In another aspect of the embodiments, the molecule is a small molecule. In a further aspect of the embodiments, the molecule is a polynucleotide.

Methods of increasing the amount of polynucleotide in a cell are known in the art and can be modified for increasing the amount of a polynucleotide encoding gene. In one aspect, the polynucleotide can be introduced to the cell and expressed by a gene delivery vehicle that can include a suitable expression vector.

Suitable expression vectors are well-known in the art, and include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory elements and may control the transcription of the nucleic acid sequence of interest. As used herein, a vector need not be capable of replication in the ultimate target cell or subject. The term vector may include expression vector and cloning vector.

Methods of down-regulating a gene (e.g., decreasing the biological activity or inhibiting a gene product) are known in the art. Non-limiting examples include mutating the gene, deleting part or whole of the sequence of the gene, or inhibiting the gene with siRNA, dsRNA, miRNA, antisense polynucleotide, ribozymes, triplex polynecleotide, antibody, or an antibody variant.

"Short interfering RNAs" (siRNA) refer to double-stranded RNA molecules (dsRNA), generally, from about 10 to about 30 nucleotides in length that are capable of mediating RNA interference (RNAi). "RNA interference" (RNAi) refers to sequence-specific or gene specific suppression of gene expression (protein synthesis) that is mediated by short interfering RNA (siRNA). As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA. A siRNA may be chemically modified to increase its stability and safety.

"Double stranded RNAs" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

"MicroRNAs" (miRNA) refer to single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

EXAMPLES

The disclosure is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1. Methods for Testing Engineered Cells

This example provides materials and methods for evaluating the genes in protein expression as shown in Example 2. 21 genes used in the experiments were cloned into pCT Mnd 4, 5, and 6. Each of the vectors was SV40 based gene expression system with a DHFR gene followed by a primary selection marker that differs for each of the vectors. Mnd4 had neomycin resistance, Mnd5 had hygromycin resistance, and Mnd6 had zeocin resistance. The Av1 gene was removed in the vectors that were used in the control (MND) experiments. The genes were cloned into each of the vectors to replace the Av1 gene denoted on the sequence maps as shown in Table 5. To quantify the presence or absence of the genes, mRNA and cDNA isolation methods were used followed by PCR.

TABLE 5

| Vector | Name of Candidate Gene | Gene Code |
| --- | --- | --- |
| Mnd4 | IDH3G | M09 |
| Mnd5 | PDP | M12 |
| Mnd6 | PKM | M17 |
| Mnd4 | PRDM1 | M18 |
| Mnd4 | AKT1 | M21 |
| Mnd4 | AKT2 | M22 |
| Mnd6 | UNC18B | M27 |
| Mnd6 | Transcarbamoylase | M280 |
| Mnd5 | Calnexin | M300 |
| Mnd6 | Carbamoyl phosphate synthetase | M310 |
| Mnd6 | Endoplasmin | M320 |
| Mnd4 | PDIA3/GRP58 | M37 |
| Mnd6 | MAPK3 | M38 |
| Mnd4 | HK1 | M07 |
| Mnd5 | Citrate Synthase | M10 |
| Mnd5 | Cdkn1b | M03 |
| Mnd6 | IL3 | M24 |
| Mnd4 | Bcl2 | M290 |
| Mnd5 | XIAP | M39 |
| Mnd5 | HK2 | M08 |
| Mnd4 | SRP14 | M25 |

TABLE 5-continued

| Vector | Name of Candidate Gene | Gene Code |
| --- | --- | --- |
| Mnd4 | Cdkn1a | M02 |
| Mnd5 | AKT3 | M23 |
| Mnd5 | Nrf2 | M13 |
| Mnd5 | Tbp | M19 |
| Mnd6 | Pfk1 | M16 |
| Mnd6 | Bip | M26 | mRNA Isolation mRNA was isolate using mRNA Catcher™ (Invitrogen, Catalog No. K1570-02). For each clone, 500 µl cell suspension containing 17,000-30,000 cells was collected from a well of 24-well plate and was spin down at 3,000 rpm in a micro centrifuge. The media removed. The cell pellet was re-suspended into 40 µl PBS. The cell suspension was transferred to a well of the mRNA Catcher™ plate. 40 µl of 2×Lysis Buffer containing 5 mM DTT was add to the well, and was mixed by pipetting up and down. After incubation at room temperature for 60 minutes, the lysates were aspirated from the well. 100 µl Wash Buffer was add to the wells followed by incubation at room temperature for 1 minute. The Wash Buffer was aspirated. The washing steps were repeated twice. Then 80 µl Elution Buffer was added into the well. The plate was incubated at 68° C. for 5 minutes and then cooled to 4° C. using a thermocycler. The eluted mRNA was transferred into a tube and stored at −80° C. until use.

cDNA Synthesis cDNA was synthesized using SuperScript™ II Reverse Transcriptase (Invitrogen Cat. No. 18064-022). For each sample, the following components were mixed: 1 µl of 300 ng/µl random primers (Invitrogen Cat. No. 48190-011); 5 µl of mRNA obtained in the above-mentioned methods; 1 µl of 10 mM dNTP Mix; and sterile, distilled water was added to a final volume of 12 µl. The mixture was heated to 65° C. for 5 min followed by quick chill on ice. Then the following components were added: 4 µl of 5×First-Strand Buffer; 2 µl of 0.1 M DTT; 1 µl of RNaseOUT™ (Invitrogen Cat. No. 40 units/µl). The mixture was then incubate at 25° C. for 2 min. 1 µl of SuperScript™ II RT was added and the tub was incubated at 25° C. for 10 min, 42° C. for 50 min, and then 70° C. for 15 min.

PCR

PCR was performed using Taq 2× Master Mix (NEB M0270). For each sample, the following components were mixed: 0.5 µl of 10 µM Forward primer; 0.5 µl of 10 µM Reverse primer; 5 µl of cDNA obtained in the above-mentioned methods; 12.5 µl of Taq 2×master mix; and Nucleae-free water was added to a final volume of 25 µl. Thermocycling conditions were as follows: Step 1: 95° C. 30 seconds; Step 2: 95° C. 30 seconds; 58° C. 30 seconds; 68° C. 1 minute; step 2 repeated for 35 cycles; Step 3: 68° C. 5 minute. PCR products were tested by electrophoresis on 1% TAE agarose gel at 100 voltage for 40 minutes. PCR primers were listed in the following table. Sgene-r was located at the 5' end of WPRE, and the forward primers were located at the 3' end of each candidate gene and were 300 bp upstream of the 5' end of WPRE.

| Gene Code | Forward primer | Reverse primer |
| --- | --- | --- |
| M2 | m2-f: CTT CGA CTT CGT CAC CGA GAC G (SEQ ID NO: 1) | sgene-r: CCA CAT AGC GTA AAA GGA GCA AC (SEQ ID NO: 24) |
| M3 | m3-f: CCT GAT CCG ACG GAC AGT CCA GC (SEQ ID NO: 2) | Same as above |

-continued

| Gene Code | Forward primer | Reverse primer |
|---|---|---|
| M7 | m7-f: AGA ACA GAG GAC TAG ACC ATC TG (SEQ ID NO: 3) | Same as above |
| M8 | m8-f: CTG GAC AGC CTC AAA GTG ACA GTG (SEQ ID NO: 4) | Same as above |
| M9 | m9-f: GCT AGC AAG TTG CAT GAT GCT AG (SEQ ID NO: 5) | Same as above |
| M10 | m10-f: TAT CCT CTT AGA GCA AGG GAA GG (SEQ ID NO: 6) | Same as above |
| M13 | m13-f: GAA CTG GAG CAA GAC TTA GGC CAC (SEQ ID NO: 7) | Same as above |
| M17 | m17-f: GCT GAG GAT GTA GAC CTC CGT GTG (SEQ ID NO: 8) | Same as above |
| M18 | m18-f: GAA GGA GAT TCT AGC TGT GGT CAG (SEQ ID NO: 9) | Same as above |
| M19 | m19-f: CAG CAG GGA TTA GTC TAT GAG CCA G (SEQ ID NO: 10) | Same as above |
| M21 | m21-f: CAG GAT GTG TAT GAG AAG AAG C (SEQ ID NO: 11) | Same as above |
| M22 | m22-f: GAA GTG GAC ACA AGG TAC TTC G (SEQ ID NO: 12) | Same as above |
| M24 | m24-f: CTG TGA GCA CCT CCG AGA TGA GAG (SEQ ID NO: 13) | Same as above |
| M25 | m25-f: AGA AAA CAA GTG TCT GTT GAG AGC (SEQ ID NO: 14) | Same as above |
| M26 | m26-f: GAA ACC ATG GAG AAA GCT GTA GAG (SEQ ID NO: 15) | Same as above |
| M27 | m27-f: CCA GGC TCA TTG TGT ACA TTG TGG (SEQ ID NO: 16) | Same as above |
| M37 | m37-f: TCC TAC CAT CTA CTT TTC ACC AGC (SEQ ID NO: 17) | Same as above |
| M38 | m38-f: CCG TAC CTG GAA CAG TAC TAT GAC (SEQ ID NO: 18) | Same as above |
| M39 | m39-f: ATC AGT ACG GAA GAG CAG CTG AGG (SEQ ID NO: 19) | Same as above |
| M290 | m290-f: GTG GAG GAA CTC TTC AGG GAT GG (SEQ ID NO: 20) | Same as above |
| M320 | m320-f: CAG CTT AAA CAT TGA CCC TGA AGC (SEQ ID NO: 21) | Same as above |
| GAPDH | GAPDH-f: GTC ATC ATC TCC GCC CCT TO (SEQ ID NO: 22) | GAPDH-r: GCG ACA TGT CAG ATC CAC AAC (SEQ ID NO: 25) |
| RTX LC | RTXLC-co-f: CCA TGT CTG TCC AAC CAC AGG TC (SEQ ID NO: 23) | RTXLC-co-r: TGA GGG AAT AAG ATG TAC CAG AGC (SEQ ID NO: 26) |

Example 2. Testing Engineered Cells

The engineered clones were tested and the results are shown in the following table (Table 6).

TABLE 6

| Gene | Hk1 | Akt1 | Akt2 | II3 | MAPK3 | XIAP | GAPDH | D12 titer/confluency | 24 well confluency |
|---|---|---|---|---|---|---|---|---|---|
| Clone 54 | .2 | .7 | .7 | 1 | .5 | 1 | 1 | 3.6478 | 5-10% |
| Clone 76 | 1.3 | 1.5 | 1.5 | 1.2 | 0 | .3 | 1 | 4.66 | 100% |
| Clone 73 | .5 | 0 | 0 | 0 | 0 | .33 | 1 | 2.7 | 70-80% |
| Average MND | 0 | 0 | 0 | 0 | 0 | 0 | 1 | 1.925 | |

Clone 54 and clone 76 had similar set of integrated candidate genes yet had wildly different growth rates. Clone 54 that included Hk1, Akt1, Akt2, IL3, MAPK3, and XIAP had a confluency of 5-10% in 24 well plates (slowest growing clone). Clone 76, which included the similar set of genes except for MAPK3, had a 100% confluency in 24 well plates (fastest growing clone). It is contemplated that this 10-20 fold difference in growth rate between the two clones was not due to the expression of MAPK3 in clone 54, since MAPK3 was known to enhance, not hinder growth. Instead, the slow growth in clone 54 may be attributed to some characteristics specific to the cells of clone 54. For example, the cells of clone 54 may not have enough energy to grow properly while maintaining enhanced protein expression.

Both clones 54 and 76 had Hk1, which would result in higher energy production. Expression of Hk1, however, is about 6 times higher in clone 76 than in clone 54. It is contemplated that expression of Hk1 may not be high enough to make a difference in energy production in clone 54. In this context, the growth enhancers (e.g., Akt1, Akt2, and 113) that are in common between the two clones had a bigger impact on the cells of clone 76 with higher energy production. Clone 73, which had a catabolic enhancement (e.g., Hk1) and a secondary enhancement (e.g., XIAP for enhancing cell survival), also had high titer.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. An isolated engineered mammalian cell comprising one or more genetic alterations resulting in increased expression or activity of hk1 (hexokinase 1), MAPK3 (mitogen-activated protein kinase 3), CAP (catabolite activator protein) and Nrf2 (nuclear factor (erythroid-derived 2)-like 2), wherein the increase is as compared to a corresponding mammalian cell without the genetic alterations.

2. The cell of claim 1, wherein the cell further comprises an exogenous polynucleotide encoding a polypeptide.

3. The cell of claim 2, wherein the polypeptide is a therapeutic protein.

4. The cell of claim 2, wherein the polypeptide is an antibody or an antibody fragment.

5. The cell of claim 1, wherein the cell is a human cell.

6. The cell of claim 1, wherein the cell is a CHO cell.

7. A composition comprising the cell of claim 2 and a cell culture medium.

8. The composition of claim 7, wherein the medium comprises a supplement selected from the group consisting of ubiquinone, aspartic acid, and rapamycin.

9. A method of producing a protein, comprising culturing the cell in the composition of claim 7 and isolating the polypeptide.

10. An isolated mammalian cell comprising one or more exogenous polynucleotides encoding hk1 (hexokinase 1), MAPK3 (mitogen-activated protein kinase 3), CAP (catabolite activator protein) and Nrf2 (nuclear factor (erythroid-derived 2)-like 2).

11. The cell of claim 10, wherein the cell is a CHO cell.

* * * * *

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttcgacttc gtcaccgaga cg                                                22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctgatccga cggacagtcc agc                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaacagagg actagaccat ctg                                               23
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggacagcc tcaaagtgac agtg                                              24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctagcaagt tgcatgatgc tag                                               23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatcctctta gagcaaggga agg                                               23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaactggagc aagacttagg ccac                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctgaggatg tagacctccg tgtg                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaggagatt ctagctgtgg tcag                                              24

```
<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagcagggat tagtctatga gccag                                          25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caggatgtgt atgagaagaa gc                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaagtggaca caaggtactt cg                                             22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgtgagcac ctccgagatg agag                                           24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agaaaacaag tgtctgttga gagc                                           24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaaaccatgg agaaagctgt agag                                           24
```

```
<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccaggctcat tgtgtacatt gtgg                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcctaccatc tacttttcac cagc                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgtacctgg aacagtacta tgac                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atcagtacgg aagagcagct gagg                                              24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtggaggaac tcttcaggga tgg                                               23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagcttaaac attgaccctg aagc                                              24

<210> SEQ ID NO 22
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtcatcatct ccgccccttc                                                   20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccatgtctgt cccaacacag gtc                                               23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccacatagcg taaaggagc aac                                                23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcgacatgtc agatccacaa c                                                 21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgagggaata agatgtacca gagc                                              24
```